(12) United States Patent
Jung et al.

(10) Patent No.: US 12,053,467 B2
(45) Date of Patent: Aug. 6, 2024

(54) METHOD OF TREATING FIBROSIS

(71) Applicant: NovMeta Pharma Co., Ltd., Seoul (KR)

(72) Inventors: Hoe Yune Jung, Pohang-si (KR); Jong Su Jeon, Gyeongsangbuk-do (KR); Do Hyun Lee, Gyeongsangbuk-do (KR); Heon Jong Lee, Incheon-si (KR)

(73) Assignee: NovMeta Pharma Co., Ltd., Seoul (KR)

( * ) Notice: Subject to any disclaimer, the term of this patent is extended or adjusted under 35 U.S.C. 154(b) by 110 days.

(21) Appl. No.: 17/126,274

(22) Filed: Dec. 18, 2020

(65) Prior Publication Data

US 2022/0193073 A1 Jun. 23, 2022

(51) Int. Cl.
*A61K 31/4985* (2006.01)
*A61K 33/30* (2006.01)
*A61P 11/00* (2006.01)
*A61P 19/04* (2006.01)

(52) U.S. Cl.
CPC .......... *A61K 31/4985* (2013.01); *A61K 33/30* (2013.01); *A61P 11/00* (2018.01); *A61P 19/04* (2018.01)

(58) Field of Classification Search
None
See application file for complete search history.

(56) References Cited

U.S. PATENT DOCUMENTS

| | | | |
|---|---|---|---|
| 6,090,780 A | 7/2000 | Prasad | |
| 7,202,279 B1 * | 4/2007 | Kozikowski | C07D 487/04 514/661 |
| 10,683,300 B2 | 6/2020 | Olmstead et al. | |
| 2007/0161640 A1 | 7/2007 | Kozikowski et al. | |
| 2009/0004291 A1 | 1/2009 | Song et al. | |
| 2009/0297616 A1 * | 12/2009 | Posten | A61K 9/0014 424/490 |
| 2010/0144624 A1 | 6/2010 | Sinisterramillán et al. | |
| 2013/0331344 A1 | 12/2013 | Tsuruoka et al. | |
| 2020/0017509 A1 * | 1/2020 | Olmstead | C07D 487/04 |
| 2020/0237815 A1 | 7/2020 | Martin | |

FOREIGN PATENT DOCUMENTS

| | | |
|---|---|---|
| JP | 2003-525850 A | 9/2003 |
| JP | 2004-518614 A | 6/2004 |
| JP | 2007-500747 A | 1/2007 |
| JP | 2011-521956 A | 7/2011 |
| JP | 2013-537195 A | 9/2013 |
| JP | 2018-510910 A | 4/2018 |
| JP | 2022-528087 A | 6/2022 |
| JP | 2022-528857 A | 6/2022 |
| KR | 10-2010-0014736 A | 2/2010 |
| KR | 10-2010-0127728 A | 12/2010 |
| KR | 10-2012-0055095 A | 5/2012 |
| KR | 10-2012-0055096 A | 5/2012 |
| KR | 10-2013-0006170 A | 1/2013 |
| KR | 10-2016-0040452 | 4/2016 |
| KR | 10-1617584 B1 | 5/2016 |
| KR | 10-1734986 A | 5/2017 |
| KR | 1020180008305 * | 1/2018 |
| KR | 10-2133151 | 7/2020 |
| KR | 10-2140910 | 8/2020 |
| WO | 95/29675 A1 | 11/1995 |
| WO | 02/01956 A1 | 1/2002 |
| WO | 2008/109445 A1 | 9/2008 |
| WO | 2018/012901 A1 | 1/2018 |
| WO | WO-2018094023 A2 * | 5/2018 .......... A61K 31/198 |
| WO | 2020/013974 A1 | 1/2020 |

OTHER PUBLICATIONS

Minelli, A. et al. "Focus on cyclo(His-Pro) . . . " Amino Acids, 35, 283-289, 2008.*
Sible (Wound Rep. Regen., 1994, 2(1), 3-19) (Year: 1994).*
Lin et al. (Nutrients, 2018, 10, 16, p. 1-20) (Year: 2018).*
Merriam-Webster online dictionary "aberrant" definition, accessed 2023, no pagination, https://www.merriam-webster.com/dictionary/aberrant.*
Grotteli et al. (Int. J. Mol. Sci., 2016, 17(8), accessed MDPI, p. 1-14).*
Nabih El-Shazly et al. (Int. J. of Neph. and Renovas. Dis., 2015, 8, 159-163).*
Jinde et al. (Am. J. of Kidney Diseases, 2001, 38(4), 761-769).*
A.P. Kakkar, "Isolation and Characterization of Ciprofloxacin-HCL Crystals," Drug Development and Industrial Pharmacy, 1997, Vo. 23, No. 11, pp. 1063-1067 (5 pages total).
Silvia Grottelli et al., "The Role of Cyclo(His-Pro) in Neurodegeneration", Int. J. Mol. Sci., 2016, vol. 17, No. 1332, pp. 23-31 (16 pages total).
Chao-Sheng Lo et al., "Atrial Natriuretic Peptide Attenuates High Glucose-Activated Transforming Growth Factor-β, Smad and Collagen Synthesis in Renal Proximal Tubular Cells", Journal of Cellular Biochemistry, 2008, vol. 109, pp. 1999-2009 (11 pages total).
Latha Muniappan et al., "Calpain Inhibition Attenuates Adipose Tissue Inflammation and Fibrosis in Diet-induced Obese Mice", Scientific Reports, 2017, vol. 7, No. 14398, pp. 1-15 (15 pages total).
Fumiko Nakazeki et al., "Loss of periostin ameliorates adipose tissue inflammation and fibrosis in vivo", Scientific Reports, 2018, vol. 8, No. 8553, pp. 1-14 (14 pages total).
Jeffrey E. Pessin et al., "How Does High-Fat Diet Induce Adipose Tissue Fibrosis?", Journal of Investigative Medicine, 2012, vol. 60, No. 8, pp. 1147-1150 (5 pages total).
Matteo Rosselli et al., "The Metabolic Syndrome and Chronic Liver Disease", Current Pharmaceutical Design, 2014, vol. 20, pp. 5010-5024 (15 pages total.
Simon Schenk et a., "Insulin sensitivity: modulation by nutrients and inflammation", The Journal of Clinical Investigation, 2008, vol. 118, No. 9, pp. 2992-3002 (12 pages total).

(Continued)

*Primary Examiner* — Erin E Hirt
(74) *Attorney, Agent, or Firm* — Sughrue Mion, PLLC

(57) ABSTRACT

A new use of a cyclo(His-Pro) is disclosed. In particular, a method for treating fibrosis and/or inflammation which includes administering an effective amount of an isolated cyclo (His-Pro) to a subject in need thereof is disclosed.

13 Claims, 14 Drawing Sheets

Specification includes a Sequence Listing.

(56) References Cited

OTHER PUBLICATIONS

Kai Sun et al., "Adipose tissue remodeling and obesity", The Journal of Clinical Investigation, 2011, vol. 121, No. 6, pp. 2094-2101 (9 pages total).
Julien Ternacle et al., "Short-term high-fat diet compromises myocardial function: a radial strain rate imaging study", European Heart Journal—Cardiovascular Imaging, 2017, vol. 18, pp. 1283-1291 (9 pages total).
Elena Ulasova et al., "Loss of interstitial collagen causes structural and functional alterations of cardiomyocyte subsarcolemmal mitochondria in acute volume overload", Journal of Molecular and Cellular Cardiology, 2011, vol. 50, pp. 147-156 (10 pages total).
Kandy T. Velazquez et al., "miR155 deficiency aggravates high-fat diet-induced adipose tissue fibrosis in male mice", Physiological Reports, 2017, vol. 5, Issue 18, e13412, pp. 1-11 (11 pages total).
Lijun Wang et al., "Berberine alleviates adipose tissue fibrosis by inducing AMP-activated kinase signaling in high-fat diet-induced obese mice", Biomedicine & Pharmacotherapy, 2018, vol. 105, pp. 121-129 (9 pages total).
Davina Wu et al., "Eosinophils sustain adipose alternatively activated macrophages associated with glucose homeostasis", Science, 2011, vol. 332, No. 6026, pp. 243-247 (10 pages total).
Ying Xia et al., "Characterization of the inflammatory and fibrotic response in a mouse model of cardiac pressure overload", Histochem Cell Biol, 2009, vol. 131, pp. 471-481 (11 pages total).
Zhou Xu et al., "Bixin ameliorates high fat diet-induced cardiac injury in mice through inflammation and oxidative stress suppression", Biomedicine & Pharmacotherapy, 2017, vol. 89, pp. 991-1004 (14 pages total).
Yi-Chao Zhao et al., "Nuclear receptor retinoid-related orphan receptor a deficiency exacerbates high-fat diet-induced cardiac dysfunction despite improving metabolic abnormality", Biochimica et Biophysica Acta, 2017, vol. 1863, pp. 1991-2000 (10 pages total).
Michele Cavalera et al., Obesity, metabolic dysfunction and cardiac fibrosis: pathophysiologic pathways, molecular mechanisms and therapeutic opportunities, Translational Research, 2014, doi: 10.1016/j.trsl.2014.05.001 (36 pages total).
Hong-Jun Chen et al., "Actein ameliorates hepatic steatosis and fibrosis in high fat diet-induced NAFLD by regulation of insulin and leptin resistant", Biomedicine & Pharmacotherapy, 2018, vol. 97, pp. 1386-1396 (11 pages total).
A. De Vries et al., "High-fat feeding redirects cytokine responses and decreases allergic airway eosinophilia", Clinical & Experimental Allergy, 2009, vol. 39, pp. 731-739 (9 pages total).
Stefan Fichtner-Feigl et al., "IL-13 signaling through the IL-13α2 receptor is involved in induction of TGF-β1 production and fibrosis", Nature Medicine, 2006, vol. 12, No. 1, pp. 99-106 (9 pages total).
Xiao Na Ge et al., "High-fat diet promotes lung fibrosis and attenuates airway eosinophilia after exposure to cockroach allergen in mice", Exp Lung Res., 2013, vol. 39, No. 9, pp. 365-378 (21 pages total).
Meilin Hu et al., "The Role of Berberine in the Prevention of HIF-1α Activation to Alleviate Adipose Tissue Fibrosis in High-Fat-Diet-Induced Obese Mice", Evidence-Based Complementary and Alternative Medicine, 2018, vol. 2018, Article ID 4395137, pp. 1-12 (13 pages total).
Alfred J. Kaltman et al., "Role of Circulatory Congestion in the Cardiorespiratory Failure of Obesity", The American Journal of Medicine, 1976, vol. 60, pp. 645-653 (9 pages total).
In Hee Kim et al., "Aging increases the susceptibility of hepatic inflammation, liver fibrosis and aging in response to high-fat diet in mice", Age, 2016, vol. 38, pp. 291-302 (12 pages total).
Ping Kong et al., "The Pathogenesis of Cardiac Fibrosis", Cell Mol Life Sci., 2014, vol. 71, No. 4, pp. 549-574 (43 pages total).
Eun-Young Kwon et al., "Luteolin Targets the Toll-Like Receptor Signaling Pathway in Prevention of Hepatic and Adipocyte Fibrosis and Insulin Resistance in Diet-Induced Obese Mice", Nutrients, 2018, vol. 10, No. 1415, pp. 1-17 (17 pages total).
Andoni Lancha et al., "Osteopontin Deletion Prevents the Development of Obesity and Hepatic Steatosis via Impaired Adipose Tissue Matrix Remodeling and Reduced Inflammation and Fibrosis in Adipose Tissue and Liver in Mice", PLoS ONE, 2014, vol. 9, Issue 5, e98398, pp. 1-15 (15 pages total).
Chun Geun Lee et al., "Interleukin-13 Induces Tissue Fibrosis by Selectively Stimulating and Activating Transforming Growth Factor β1", J. Exp. Med., 2001, vol. 194, No. 6, pp. 809-821 (13 pages total).
Wei Li et al., "Folic acid prevents cardiac dysfunction and reduces myocardial fibrosis in a mouse model of high-fat diet-induced obesity", Nutrition & Metabolism, 2017, vol. 14, No. 68, pp. 1-8 (8 pages total).
International Search Report of PCT/KR2020/004354 dated Jul. 17, 2020 [PCT/ISA/210].
Tsuburai et al., "Adenovirus-Mediated Transfer and Overexpression of Heme Oxygenase 1 cDNA in Lung Prevents Bleomycin-Induced Pulmonary Fibrosis via a Fas-Fas Ligand-Independent Pathway," Human Gene Therapy, 2002, vol. 13, pp. 1945-1960.
Silvia Grottelli et al., "Cyclo(His-Pro) inhibits NLRP3 inflammasome cascade in ALS microglial cells", Molecular and Cellular Neuroscience, 2019, vol. 94, pp. 23-31 (13 pages total).
International Search Report of PCT/KR2020/004343 dated Jul. 17, 2020 [PCT/ISA/210].
Zhang et al., "Strategies for preventing peritoneal fibrosis in peritoneal dialysis patients: new insights based on peritoneal inflammation and angiogenesis", Front. Med., 2017, vol. 11, No. 3, pp. 349-358 (10 pages total).
Extended European Search Report dated Jan. 16, 2023 from the European Patent Office in EP Application No. 20776685.8.
Fang Tian, et al., "Factors affecting crystallization of hydrates", JPP, 2010, vol. 62, pp. 1534-1546.
International Search Report issued Aug. 28, 2019 in International Application No. PCT/US2019/038391.
International Preliminary Report on Patentability issued Jan. 12, 2021 in International Application No. PCT/US2019/038391.
"AKI: Mechanisms—Primary Injury and Repair—II", J Am Soc Nephrol: Kidney Week Edition (Abstract Supplement), 2019, vol. 30, p. 786 (1 page).
Kwang Bon Koo, et al., "Protective Effect of Cyclo(His-Pro) on Streptozotocin-Induced Cytotoxicity and Apoptosis In Vitro", J. Microbiol. Biotechnol., 2011, vol. 21, No. 2, pp. 218-227.
International Searching Authority, International Search Report mailed Mar. 22, 2022 in Application No. PCT/IB2021/061882.
Office Action issued Nov. 18, 2023 in Chinese Application No. 201980046575.8.

* cited by examiner

SEQUENCE LISTING

<160> NUMBER OF SEQ ID NOS: 14

<210> SEQ ID NO 1
<211> LENGTH: 21

-continued

```
<212> TYPE: DNA
<213> ORGANISM: Artificial Sequence
<220> FEATURE:
<223> OTHER INFORMATION: Forward Primer (Collagen 1)

<400> SEQUENCE: 1
gcctcagaag aactggtaca t                                            21

<210> SEQ ID NO 2
<211> LENGTH: 20
<212> TYPE: DNA
<213> ORGANISM: Artificial Sequence
<220> FEATURE:
<223> OTHER INFORMATION: Reverse Primer (Collagen 1)

<400> SEQUENCE: 2
atccatcggt catgctctct                                              20

<210> SEQ ID NO 3
<211> LENGTH: 20
<212> TYPE: DNA
<213> ORGANISM: Artificial Sequence
<220> FEATURE:
<223> OTHER INFORMATION: Forward Primer (Collagen 3)

<400> SEQUENCE: 3
agtcaaggag aaagtggtcg                                              20

<210> SEQ ID NO 4
<211> LENGTH: 19
<212> TYPE: DNA
<213> ORGANISM: Artificial Sequence
<220> FEATURE:
<223> OTHER INFORMATION: Reverse Primer (Collagen 3)

<400> SEQUENCE: 4
ccagggaaac ccatgacac                                               19

<210> SEQ ID NO 5
<211> LENGTH: 20
<212> TYPE: DNA
<213> ORGANISM: Artificial Sequence
<220> FEATURE:
<223> OTHER INFORMATION: Forward Primer (Collagen 4)

<400> SEQUENCE: 5
cggtacacag tcagaccatt                                              20

<210> SEQ ID NO 6
<211> LENGTH: 20
<212> TYPE: DNA
<213> ORGANISM: Artificial Sequence
<220> FEATURE:
<223> OTHER INFORMATION: Reverse Primer (Collagen 4)

<400> SEQUENCE: 6
catcacgaag gaatagccga                                              20

<210> SEQ ID NO 7
<211> LENGTH: 21
<212> TYPE: DNA
<213> ORGANISM: Artificial Sequence
<220> FEATURE:
<223> OTHER INFORMATION: Forward Primer (Fibronectin)

<400> SEQUENCE: 7
```

```
atgtaccota tgtaccgctt c                                         21

<210> SEQ ID NO 8
<211> LENGTH: 18
<212> TYPE: DNA
<213> ORGANISM: Artificial Sequence
<220> FEATURE:
<223> OTHER INFORMATION: Reverse Primer (Fibronectin)

<400> SEQUENCE: 8
gtgtggtggt ggttggag                                             18

<210> SEQ ID NO 9
<211> LENGTH: 23
<212> TYPE: DNA
<213> ORGANISM: Artificial Sequence
<220> FEATURE:
<223> OTHER INFORMATION: Forward Primer (alphaSMA)

<400> SEQUENCE: 9
aataacacag agagacagac ttg                                       23

<210> SEQ ID NO 10
<211> LENGTH: 21
<212> TYPE: DNA
<213> ORGANISM: Artificial Sequence
<220> FEATURE:
<223> OTHER INFORMATION: Reverse Primer (alphaSMA)

<400> SEQUENCE: 10
cttggatacc cttggcttta g                                         21

<210> SEQ ID NO 11
<211> LENGTH: 20
<212> TYPE: DNA
<213> ORGANISM: Artificial Sequence
<220> FEATURE:
<223> OTHER INFORMATION: Forward Primer (TGFbeta)

<400> SEQUENCE: 11
cctgagtggc tgtcttttga                                           20

<210> SEQ ID NO 12
<211> LENGTH: 21
<212> TYPE: DNA
<213> ORGANISM: Artificial Sequence
<220> FEATURE:
<223> OTHER INFORMATION: Reverse Primer (TGFbeta)

<400> SEQUENCE: 12
aatcgaaagc cctgtattcc g                                         21

<210> SEQ ID NO 13
<211> LENGTH: 19
<212> TYPE: DNA
<213> ORGANISM: Artificial Sequence
<220> FEATURE:
<223> OTHER INFORMATION: Forward Primer (beta-Actin)

<400> SEQUENCE: 13
gcgagaagat gacccagat                                            19

<210> SEQ ID NO 14
<211> LENGTH: 18
<212> TYPE: DNA
<213> ORGANISM: Artificial Sequence
```

```
<220> FEATURE:
<223> OTHER INFORMATION: Reverse Primer (beta-Actin)

<400> SEQUENCE: 14
atcacgatgc cagtggta                                              18
```

METHOD OF TREATING FIBROSIS

SEQUENCE LISTING

The instant application contains a Sequence Listing which has been submitted electronically in ASCII format and is hereby incorporated by reference in its entirety. Said ASCII copy, created on Dec. 31, 2020, is named Q259365 Substitute Sequence Listing.txt and is 3,002 bytes in size.

TECHNICAL FIELD

The present disclosure is directed to a composition effective in treating and/or preventing inflammation and fibrosis. The present disclosure also is directed to a method for treating and/or preventing inflammation and fibrosis.

BACKGROUND

Fibrosis, also known as fibrotic scarring, is a pathological wound healing in which connective tissue replaces normal parenchymal tissue to the extent that it goes unchecked, leading to considerable tissue remodelling and the formation of permanent scar tissue.

Repeated injuries, chronic inflammation and repair are susceptible to fibrosis where an accidental excessive accumulation and deposition of extracellular matrix (ECM) components such as the collagen and fibronectin (FN) is produced by fibroblasts, leading to the formation of a permanent fibrotic scar.

Uncontrollable wound-healing responses, including acute and chronic inflammation, angiogenesis, activation of resident cells, and ECM remodeling, are thought to be involved in the pathogenesis of fibrosis. TGF-β is the prototype fibrotic cytokine that is increased in fibrotic organs and contributes to the development of fibrosis by stimulating the synthesis of ECM molecules, activating fibroblasts to α-smooth muscle actin (α-SMA)-expressing myofibroblasts, and downregulating matrix metalloproteinases (MMPs). Wynn and Ramalingam, Nat. Med. 18(7), pp. 1028-1040 (2012), doi:10.1038/nm.2807.

Activation of liver myofibroblasts is responsible for the development of liver fibrosis in chronic liver diseases, and it is reasonably expected that inhibiting or reversing myofibroblastic activation of different cellular origins is critical for the treatment of liver fibrosis.

A medication that would prevent progression of liver fibrosis and decrease liver inflammation would impact the management of patients with various liver disorder such as non-alcoholic steatohepatitis; hepatitis C; hepatitis B; and other chronic liver diseases afflicting adults (primary biliary cirrhosis; sclerosing cholangitis; autoimmune hepatitis; genetic hemochromatosis) and children (including biliary atresia; α-1 antitrypsin deficiency and other rare genetic disorders).

A medication that would decrease or prevent the progression of lung fibrosis would impact the healthcare of patients with Idiopathic Pulmonary Fibrosis (IPF).

It is known that inflammation contributes to the pathogenesis of most acute and chronic liver diseases1. Various factors including toxic environment (e.g., toxic or irritating fume), autoimmune condition, virus infection, metabolic syndrome can cause excessive liver injury and inflammation, which eventually results in liver dysfunction and in chronic conditions.

There is still need a new effective and safe treatment for fibrosis, including idiopathic pulmonary fibrosis, and inflammation.

Cyclo(-His-Pro) (cyclo-Hirpro or CHP), $C_{11}H_{14}N_4O_2$, has been known as an anhydrous dipeptide having the CAS Registry Number 53109-32-3. It is an endogenous cyclic dipeptide derived in vivo from the hydrolytic removal of the amino-terminal pyroglutamic acid residue of the hypothalamic thyrotropin-releasing hormone.

Rosenthal et al. (Life Sciences 70 (2001), 337-348) reported that CHP enhanced zinc absorption and uptake by muscle tissues and by intestinal segments.

U.S. Pat. No. 5,834,032 describes the use of CHP and zinc to lower insulin levels as a method for treating insulin-resistant diabetes.

U.S. Pat. No. 10,058,520 discloses the use of thyroid hormone, CHP and a zinc salt together in treating or delaying the onset of Alzheimer's disease and/or dementia in mammals.

The present inventors surprisingly found that CHP remarkably downregulating the ECM components such as fibronectin and collagens (types I, II, and III), αSMA, and TGF-β, and, reducing hydroxyproline accumulation, thus, can be effectively used in treating a fibrosis.

SUMMARY

The present disclosure provides a method for treating an inflammation and/or organ fibrosis in a subject in need thereof by administering a composition comprising a cyclo(-His-Pro) ("CHP") to the subject.

In an embodiment, the method of treating a fibrosis in a subject in need thereof comprises administering an effective amount of a pharmaceutical composition comprising a CHP to the subject. The method may further comprise administering zinc. The CHP-comprising composition and Zn-comprising composition may be administered sequentially or simultaneously. In another embodiment, the composition comprising CHP may further comprise zinc.

In an embodiment, the composition consists essentially of a CHP. In an embodiment, the CHP-comprising composition does not include zinc.

According to an embodiment, the cylco(-His-Pro) or CHP is a crystalline cyclo(-His-Pro) hydrate ("CHP hydrate"). The term "CHP" or "cyclo(-His-Pro)" as used herein comprises anhydrous CHP, amorphous CHP, crystalline CHP, and a CHP hydrate. A CHP hydrate with improved stability is disclosed in US 2020-0017509A1 (U.S. application Ser. No. 16/448,083), of which the entire content is incorporated herein by reference.

In an embodiment, the CHP hydrate may comprise X-ray diffraction peaks in 2θ values of about 13.5° - about 13.9°, about 16.8° - about 17.2°, and about 27.1° - about 27.5°.

In another embodiment, the CHP hydrate may comprise three or more X-ray diffraction peaks in 2θ values selected from about 9.8° - about 10.2°, about 13.5° - about 13.9°, about 16.8° - about 17.2°, about 17.9° - about 18.3° - about 20.0° - about 20.2°, and - about 27.1° - about 27.5° - about 27.5°.

In an embodiment, the CHP hydrate is stable at typical room temperature storage conditions for about 6 months, or about 12 months, or about 18 months, or about 24 months, or about 36 months.

In another embodiment, the CHP hydrate is substantially pure. In some embodiments, the CHP hydrate material is at least about 90% pure, or at least about 95%, 96%, 97%, 98%, 99%, or 100% pure.

In another embodiment, the CRP hydrate material may be characterized by at least two of the following:
(a) an X-ray powder diffractogram comprising at least two peaks in 2θ values chosen from the following list: about 9.8° - about 10.2°, about 13.5° - about 13.9°, about 16.8° - about 17.2°, about 17.9° - about 18.3°, about 20.0° - about 20.2°, and about 27.1° - about 27.5°;
(b) pKa of about 6.4;
(c) birefringent with a fragmented, rod-like morphology when analyzed by polarized light microscopy;
(d) an initial weight loss of about 6.5% (0.9 equivalent of water), followed by sample degradation at about 280° C. when analyzed by thermogravimetric analysis technique;
(e) an endotherm with an onset of about 99° C. and a peak at about 102° C. in the first heat cycle of DSC;
(f) start of dehydration below about 10% relative humidity (RH), loss of about 5.8 wt % from 10 to 0% RH (0.8 equivalent of water) and hydration from 0 to about 40% RH in the 40° C. dynamic vapor sorption analysis;
(g) start of dehydration below about 20% RH, loss of about 6.1 wt % from about 20 to 0% RH (0.8 equivalent of water) and rehydration from 0 to about 40% RH in the 50° C. dynamic vapor sorption analysis; and
(h) start of dehydration below about 20% RH, loss of about 7 wt % from about 20 to 0% RH (1.0 equivalent of water), and rehydration from 0 to about 40% RH in the 60° C. dynamic vapor sorption analysis.

In an embodiment, the composition comprising a CHP may further include a zinc metal, an organic or inorganic salt of zinc, a zinc compound, or a zinc ion.

In an embodiment, the composition consists essentially of a CHP. According to this embodiment, the composition comprising a CHP does not include a zinc metal, an organic or inorganic salt of zinc, a zinc compound, or a zinc ion.

In an embodiment, the composition consists essentially of (a) a CHP and (b) a zinc metal, an organic or inorganic salt of zinc, a zinc compound, or a zinc ion.

In an embodiment, the compositions discussed above are a pharmaceutically acceptable composition and may comprise a pharmaceutically acceptable carriers or excipients in addition to the above-discussed CHP and/or the zinc component.

In an embodiment, the individual in need of such treatment is an individual who has been diagnosed with or who is suspected of having fibrosis and/or inflammation. In one aspect, the individual suffers from an idiopathic pulmonary fibrosis.

In an embodiment, the effective amount of the composition comprising a CHP is administered to the individual on a schedule or regimen.

In an embodiment, the schedule or regimen is daily administration for a period of time.

In an embodiment, the period of time is daily for about two weeks, daily for about three weeks, daily for about four weeks, daily for about five weeks, daily for about six weeks, daily for about seven weeks, daily for about eight weeks, daily for about nine weeks, daily for about ten weeks, daily for about two months, daily for about three months, daily for about four months, daily for about five months, or daily for about six months.

In an embodiment, the effective amount of the CHP is administered until the severity of one or more symptoms associated with a fibrosis, specifically has reduced or improved.

In an embodiment, the subject may have lung fibrosis. In other embodiments, the subject has idiopathic pulmonary fibrosis, fibrosis as a result of Graft-Versus-Host Disease (GVHD), endomyocardial fibrosis, uterine fibrosis, myelofibrosis, retroperitoneal fibrosis, scarring after surgery, asthma, aberrant wound healing, glomerulonephritis, and/or multifocal fibrosclerosis. In an embodiment, the subject with lung fibrosis does not have an autoimmune disease.

In another aspect, the invention provides a method for treating an inflammatory disease in a subject in need thereof comprising administering to the subject an effective amount of a CHP or a pharmaceutical composition comprising the CHP. In one embodiment, the disease is selected from the group consisting of alcoholic liver disease, non-alcoholic steato-hepatitis (NASH), autoimmune hepatitis, chronic hepatitis C, chronic hepatitis B, primary biliary cirrhosis, secondary biliary cirrhosis, sclerosing cholangitis, alpha-1-antitrypsin deficiency, Wilson's disease, biliary atresia, idiopathic pulmonary fibrosis, radiation-induced pneumonitis, chronic obstructive pulmonary disease, lung emphysema, lung chronic infections and/or inflammation, glomerulonephritis, interstitial-tubular fibrosis.

In embodiments, with regard to the above methods, the composition is administered daily for a period of 2-5 weeks, 2-6 weeks, 3-7 weeks, 3-8 weeks, 4-9 weeks, 4-10 weeks, 5-10 weeks, 6-11 weeks, 6-12 weeks, or 3-6 months.

In embodiments, with regard to the above methods, the effective amount of a CRP may be for example in a range of about 1-10 mg/day, about 10-50 mg/day, about 50-100 mg/day, about 100-150 mg/day, about 150-200 mg/day, about 200-300 mg/day, about 300-400 mg/day, about 400-500 mg/day, about 500-600 mg/day, about 600-700 mg/day, about 700-800 mg/day, about 800-900 mg/day, about 900-1000 mg/day, about 1000-1100 mg/day, about 1100-1200 mg/day, about 1200-1300 mg/day, about 1300-1400 mg/day, about 1400-1500 mg/day, about 1500-1600 mg/day, about 1600-1700 mg/day, about 1700-1800 mg/day, about 1800-1900 mg/day, about 1900-2000 mg/day, about 2000-2100 mg/day, about 2100-2200 mg/day, about 2200-2300 mg/day, about 2300-2400 mg/day, about 2400-2500 mg/day, about 2500-2600 mg/day, about 2600-2700 mg/day, about 2700-2800 mg/day, about 2800-2900 mg/day, or about 2900-3000 mg/day, calculated in term of anhydrous CHP.

In embodiments, with regard to the above methods, the effective amount of a CHP may be for example in a range of about 0.001-0.005 mg/kg, about 0.005-0.01 mg/kg, about 0.01-0.02 mg/kg, about 0.02-0.04 mg/kg, about 0.04-0.06 mg/kg, about 0.06-0.08 mg/kg, about 0.08-1 mg/kg, about 1-5 mg/kg, about 5-6 mg/kg, about 6-7 mg/kg, about 7-8 mg/kg, about 8-10 mg/kg, about 10-15 mg/kg, about 15-20 mg/kg, about 20-25 mg/kg, about 25-30 mg/kg, about 30-35 mg/kg, about 35-40 mg/kg, about 40-45 mg/kg, about 45-50 mg/kg, about 50-100 mg/kg, about 100-150 mg/kg, about 150-200 mg/kg, about 200-300 mg/kg, about 300-400 mg/kg, about 400-500 mg/kg, about 500-600 mg/kg, about 600-700 mg/kg, about 700-800 mg/kg, about 800-900 mg/kg, about 900-1000 mg/kg, about 1000-1100 mg/kg, about 1100-1200 mg/kg, about 1200-1300 mg/kg, about 1300-1400 mg/kg, about 1400-1500 mg/kg, about 1500-1600 mg/kg, about 1600-1700 mg/kg, about 1700-1800 mg/kg, about 1800-1900 mg/kg, about 1900-2000 mg/kg, about 2000-2100 mg/kg, about 2100-2200 mg/kg, about 2200-2300 mg/kg, about 2300-2400 mg/kg, about 2400-2500 mg/kg, about 2500-2600 mg/kg, about 2600-2700 mg/kg, about 2700-2800 mg/kg, 2 about 800-2900 mg/kg, or about 2900-3000 mg/kg, calculated in term of anhydrous CHP.

In the above ranges, the amount of CHP is expressed based on anhydrous CHP. Therefore, when a CHP hydrate is used as the CHP in the composition, the amount could be converted accordingly.

BRIEF DESCRIPTION OF THE DRAWINGS

The foregoing features of embodiments will be more readily understood by reference to the following detailed description, taken with reference to the accompanying drawings, in which.

DETAILED DESCRIPTION

Figure 1:
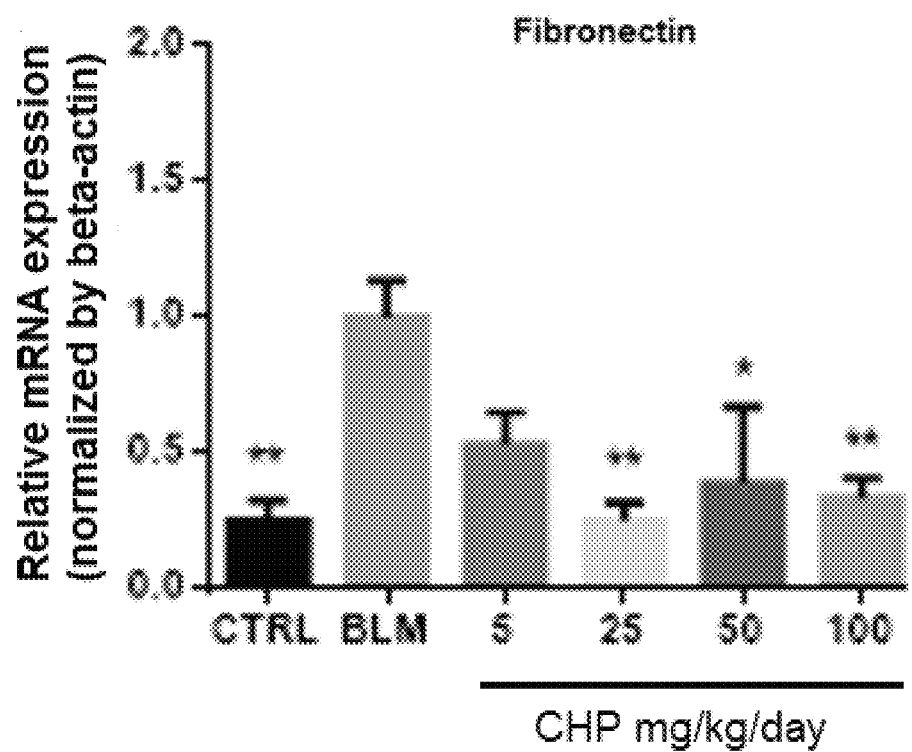
FIG. 1 shows the relative mRNA expression levels of fibronectin in bleomycin (BLM)-induced pulmonary fibrosis ICR mice. The fibronectin mRNA expression level (BLM bar) in the ICR mice injected with bleomycin to induce pulmonary fibrosis is set 1.0. CTRL is a control mice which did not receive bleomycin. 5, 25, 50, and 100 CHP mg/kg bars show the relative fibronectin mRNA expression levels in the BLM-injected ICR mice. The results show that 5, 25, 50, and 100 mg/kg CHP significantly reduces the fibronectin expression in pulmonary fibrosis animal model.

The various aspects and embodiments will now be fully described herein. These aspects and embodiments may, however, be embodied in many different forms and should not be construed as limiting; rather, these embodiments are provided so the disclosure will be thorough and complete, and will fully convey the scope of the present subject matter to those skilled in the art. All publications, patents and patent applications cited herein, whether supra or infra, are hereby incorporated by reference in their entirety.

Definitions

Unless defined otherwise, all terms and phrases used herein include the meanings that the terms and phrases have attained in the art, unless the contrary is clearly indicated or clearly apparent from the context in which the term or phrase is used. Although any methods and materials similar or equivalent to those described herein can be used in the practice or testing of the present invention, particular methods and materials are now described.

Unless otherwise stated, the use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value or range. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Consequently, recitation of ranges of values herein are merely intended to serve as a shorthand method of referring individually to each separate value falling within the range, and each separate value is incorporated into the specification as if it were individually recited herein. In an aspect, the word "about" as used in referring to a numerical value is intended to include 10%, 9%, 8%, 7%, 6%, 5%, 4%, 3%, 2%, or 1% variance from the numerical value(s).

The term "animal" used here indicates living multicellular vertebrate organisms, a category that includes, for example, mammals and birds. The term mammal includes both human and non-human mammals. Similarly, the term "subject" includes both human and veterinary subjects.

The term "active agent" or "drug," as used herein, refers to any chemical that elicits a biochemical response when administered to a human or an animal. The drug may act as a substrate or product of a biochemical reaction, or the drug may interact with a cell receptor and elicit a physiological response, or the drug may bind with and block a receptor from eliciting a physiological response.

The phrase "consists essentially of" used herein with regard to a composition or formulation means that the composition or formulation contains the listed compound(s) as sole active ingredient(s) and may additionally contain a pharmaceutically acceptable inert additive(s), excipient(s), or carrier(s). Such inert additives, excipients, or carriers are known in the art.

The term "fibrosis" is the formation or development of excess fibrous connective tissue in an organ or tissue as a reparative or reactive process, as opposed to a formation of fibrous tissue as a normal constituent of an organ or tissue. Skin and lungs are susceptible to fibrosis. Exemplary fibrotic conditions are scleroderma idiopathic pulmonary fibrosis, morphea, fibrosis as a result of Graft-Versus-Host Disease (GVHD), keloid and hypertrophic scar, and subepithelial fibrosis, endomyocardial fibrosis, uterine fibrosis, myelofibrosis, retroperitoneal fibrosis, nephrogenic systemic fibrosis, scarring after surgery, asthma, cirrhosis/liver fibrosis, aberrant wound healing, glomerulonephritis, and multifocal fibrosclerosis.

The term "idiopathic pulmonary fibrosis" is a condition also known as cryptogenic fibrosing alveolitis (CFA) that is a chronic, progressive form of lung disease characterized by fibrosis of the supporting framework (interstitium) of the lungs. By definition, the term is used only when the cause of the pulmonary fibrosis is unknown ("idiopathic"). When lung tissue from patients with IPF is examined under a microscope by a pathologist, it shows a characteristic set of histologic/pathologic features known as usual interstitial pneumonia (UIP). UIP is characterized by progressive scarring of both lung that involves the supporting framework (interstitium) of the lung.

According to the CHEST® Foundation, development and/or severity of lung fibrosis vary from person to person, and the overall course of the disease can be unpredictable. Signs and symptoms of pulmonary fibrosis include: shortness of breath, dry cough, fatigue, weight loss, muscle and joint aching. Therefore, treatment of lung fibrosis including IPF includes, but is not limited to, a decrease in the number and/or duration of these signs and symptoms of the patient after receiving the inventive composition.

The terms "parenteral administration" and "administered parenterally" are art-recognized and refer to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal injection.

The term "inhibiting" or "treating" a disease refers to inhibiting the full development of a disease. In several examples, inhibiting a disease refers to lessening symptoms of a fibrosis, such as the formation of scar tissue or an increase in range of motion or a decrease in pain, and the term "treatment" or "treating" refers to a therapeutic intervention that ameliorates a sign or symptom of a disease or pathological condition related to the disease, such as the fibrosis.

The phrase "pharmaceutically acceptable" additives, excipients, or carriers as used herein include those well known in the art. In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional nontoxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

The term "therapeutically effective amount" or "effective amount," or "effective dose," as used herein, is the amount of the anhydrous CHP or CHP hydrate (as calculated as CHP hydrate) present in a composition described herein that is needed to provide a desired level of drug in the secretions and tissues of the airways and lungs, or alternatively, in the bloodstream of a subject to be treated to give an anticipated physiological response or desired biological effect when such a composition is administered by the chosen route of administration. The precise amount will depend upon numerous factors, for example the specific activity of the composition, the delivery device employed, the physical characteristics of the composition, its intended use, as well as patient considerations such as severity of the disease state, patient cooperation, etc., and can be determined by one skilled in the art based upon the information provided herein.

The terms "increased," or "increase" are used herein to generally mean an increase by a statically significant amount; in some embodiments, the terms "increased," or "increase," mean an increase of at least 10% as compared to a reference level, for example an increase of at least about 10%, at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level. Other examples of "increase" include an increase of at least 2-fold, at least 5-fold, at least 10-fold, at least 20-fold, at least 50-fold, at least 100-fold, at least 1000-fold or more as compared to a reference level.

The term "suppress" or "suppressed" are used herein generally to mean that a progress of a disease or development of symptom(s) is slowed or decreased, compared to the absence of an intervention.

The terms, "decreased" or "decrease" are used herein generally to mean a decrease by a statistically significant amount. In some embodiments, "decreased" or "decrease" means a reduction by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (e.g., absent level or non-detectable level as compared to a reference level), or any decrease between 10-100% as compared to a reference level. In the context of a marker or symptom, by these terms is meant a statistically significant decrease in such level. The decrease can be, for example, at least 10%, at least 20%, at least 30%, at least 40% or more, and is preferably down to a level accepted as within the range of normal for an individual without a given disease.

Cyclo(His-Pro) and Pharmaceutical Compositions

According to an aspect of the disclosure, CHP may be anhydrous, amorphous, crystalline, or a hydrate. A CHP hydrate comprises CHP monohydrate, CHP dihydrate, CHP hemihydrate, CHP 1.5 hydrate, and the like. Therefore, the term "CHP" as used herein is intended to encompass anhydrous CHP, CHP hydrate, amorphous CHP, and crystalline CHP. In a particular embodiment, the CHP may be a CHP monohydrate. In an embodiment, the CHP monohydrate may be in a crystalline form. In still another embodiment, the crystalline CHP monohydrate may show certain X-ray diffractive pattern as described herein.

A cyclo (-His-Pro) (CHP) is illustrated below:

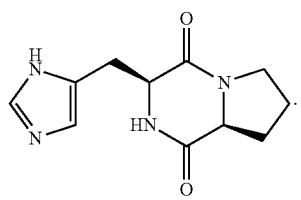 [SMILES: O=C1N[C@@H](Cc2cnc[nH]2)C(=O)N2CCC[C@@H]12]

A CHP monohydrate is illustrated below:

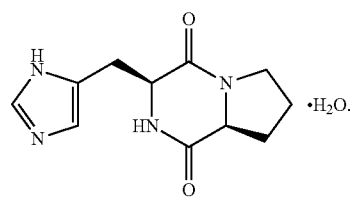 [SMILES: O=C1N[C@@H](Cc2cnc[nH]2)C(=O)N2CCC[C@@H]12]

In one embodiment, the CHP is substantially pure.

In an embodiment, the CHP is a CHP hydrate. In still another embodiment, the CHP hydrate is characterized by an XRPD diffractogram comprising peaks at about 17±0.2° and about 27.3±0.2° in 2θ.

One embodiment of substantially pure CHP hydrate is characterized by an X-ray powder diffractogram comprising at least three peaks chosen from the following list: 13.7, 17, 18.1, 20.2 and 27.3 degrees (±0.2° in 2θ). Another embodiment is characterized by an XRPD diffractogram comprising at least two peaks chosen from the following list: 10, 13.7, 17, 18.1, 20.2 and 27.3 degrees (±0.2° in 2θ).

CHP synthesized from different biochemical sources, including histidine-proline-rich glycoprotein. High levels of CHP are present in many food sources, and are readily absorbed in the gut without chemical or enzymatic destruction.

CHP hydrate can be made by a process described in US application Ser. No. 16/448,083, of which content is incorporated herein by reference, in its entirety.

CHP can be used as a substantially pure form of CHP in amorphous or crystalline form or a substantially pure form of CHP hydrate crystalline, or a mixture of CHP and CHP hydrate, as described in US application Ser. No. 16/448,083, of which the entire content is incorporated herein by reference. The term "CHP" as used herein is meant to encompass anhydrous CHP, CHP hydrate, a crystalline CHP hydrate (Pattern I, Pattern II, and a mixture thereof), amorphous CHP, and a mixture thereof. And, the term "CHP" and "cyclo-Hispro" and "CHP/CHP hydrate" are interchangeably herein used to indicate the CHP, CHP hydrate, a crystalline CHP hydrate (Pattern I, Pattern II, and a mixture thereof), and a mixture thereof, unless a specific form of CHP is intended by a specific reference to a certain form. In another embodiment, CHP is a crystalline CHP hydrate. In an embodiment, CHP hydrate is a CHP monohydrate. In some embodiment, CHP is a mixture of crystalline CHP hydrates.

A composition suitable for treating a fibrosis or inflammation comprises a CHP as an active ingredient. The composition may comprise a pharmaceutically acceptable carrier or excipient, which is known in the art. The composition may further comprise zinc. The CHP may be a CHP hydrate. The composition comprising the CHP and zinc may be administered to treat fibrosis. The composition may be administered to decrease the amount or the expression of fibronectin, collagens (collagen 1, 3, and/or 4), alpha-SMA, and/or TGF-beta in a target tissue. The composition may be administered to reduce the hydroxyproline deposit in a target tissue.

A composition suitable for treating a fibrosis or inflammation may consist essentially of a CHP and may comprise a pharmaceutically acceptable carrier or excipient. The composition may be administered alone to treat fibrosis. The composition may be administered alone to decrease the amount or the expression of fibronectin, collagens (collagen 1, 3, and/or 4), alpha-SMA, and/or TGF-beta in a target tissue. The composition may be administered alone to reduce the hydroxyproline deposit in a target tissue.

Compositions intended for oral use may be prepared according to any method, and such compositions may contain one or more agents such as sweetening agents, flavoring agents, coloring agents, and/or preserving agents in order to provide pharmaceutically elegant and palatable preparations. Suitable excipients for tablets and capsules include inert diluents, such as safflower oil, lecithin, inositol, soybean shortening oil, gelatin, acacia, glycerin, titanium oxide and soybean oil. The coating of the capsules can be gelatin or a soluble polymer, as is well understood in the art. The tablets or capsules are suitable for oral administration according to a daily administration regimen.

In one embodiment, a composition comprising CHP alone as an active ingredient and a composition comprising zinc may be administered separately. These compositions may be administered simultaneously or sequentially. These compositions may be administered to treat fibrosis. The compositions may be administered to decrease the amount or the expression of fibronectin, collagens (collagen 1, 3, and/or 4), alpha-SMA, and/or TGF-beta in a target tissue. The compositions may be administered to reduce the hydroxyproline deposit in a target tissue.

The amount of zinc in the above compositions comprising zinc may range from about 0.1 to about 2000 mg, about 1 to 1000 mg, about 1 to 500 mg, about 10 to about 2000 mg, about 20 to about 1000 mg, about 20 to about 500 mg, about 50 to about 2000 mg, about 50 to 1000 mg, about 50 to 800 mg, or about 50 to 500 mg, as calculated in term of zinc cation.

In one embodiment, a CHP may be present in the same composition comprising zinc or in a different composition in amount ranging from about 0.5 to about 3000 mg, from about 1 to 2000 mg, or from about 10 to about 1000 mg. In another embodiment, the amount of CHP present in the administered pharmaceutical composition may range from about 5 to about 3000 mg, from about 50 to about 2000 mg, from about 100 to about 2000 mg, from about 50 to about 1000 mg, from about 100 to about 1000 mg, from about 150 to about 2000 mg, from about 200 to about 1000 mg, from about 50 to about 800 mg, from about 100 to about 700 mg, from about 50 to about 600 mg, or from about 100 to about 1500 mg, as calculated in term of anhydrous CHP.

Treatment Methods

In an embodiment, the CHP disclosed herein can be used to treat fibrosis or inflammation. In some embodiments, the CHP may be used to decrease fibrosis or inflammation in a subject. According to an aspect of the disclosure, the methods include administering to a subject a therapeutically effective amount of a CHP to decrease fibrosis or inflammation. In some embodiments, the CHP can be administered as a unit dose.

A suitable subject may include those with a fibrosis. In an embodiment, the subject may have lung fibrosis. In other embodiments, the subject has idiopathic pulmonary fibrosis, fibrosis as a result of Graft-Versus-Host Disease (GVHD), endomyocardial fibrosis, uterine fibrosis, myelofibrosis, retroperitoneal fibrosis, nephrogenic systemic fibrosis, scarring after surgery, asthma, cirrhosis/liver fibrosis, aberrant wound healing, glomerulonephritis, and/or multifocal fibrosclerosis. In an embodiment, the subject with lung fibrosis does not have an autoimmune disease and/or Alzheimer disease. In another embodiment, the subject with lung fibrosis is not diabetic.

According to an embodiment, the methods can include selecting a subject in need of treatment, such as a subject with a fibrotic disease, such as idiopathic pulmonary fibrosis, fibrosis as a result of Graft-Versus-Host Disease (GVHD), endomyocardial fibrosis, uterine fibrosis, myelofibrosis, retroperitoneal fibrosis, nephrogenic systemic fibrosis, scarring after surgery, asthma, cirrhosis/liver fibrosis, aberrant wound healing, glomerulonephritis, and/or multifocal fibrosclerosis. In exemplary embodiments, compositions are administered to a subject having a fibrotic disease, such as idiopathic pulmonary fibrosis, fibrosis as a result of Graft-Versus-Host Disease (GVHD), endomyocardial fibrosis, uterine fibrosis, myelofibrosis, retroperitoneal fibrosis, nephrogenic systemic fibrosis, scarring after surgery, asthma, cirrhosis/liver fibrosis, aberrant wound healing, glomerulonephritis, and/or multifocal fibrosclerosis, in an amount sufficient to reduce the fibrosis. Amounts effective for this use will depend upon the severity of the disease, the general state of the patient's health, and the robustness of the patient's immune system. In one example, a therapeutically effective amount of the compound is that which provides either subjective relief of a symptom(s) or an objectively identifiable improvement as noted by the clinician or other qualified observer.

In another aspect, the invention provides a method for inhibiting tissue fibrosis in a subject in need thereof, wherein the method comprises administering to the subject an effective amount of a CHP or a pharmaceutical composition comprising the CHP. In one embodiment, the tissue is in the liver, lung, or kidney. In one embodiment, the tissue fibrosis is associated with liver injury or liver inflammation. In one embodiment, the tissue fibrosis is associated with lung injury or lung inflammation. In one embodiment, the tissue fibrosis is associated with kidney injury or kidney inflammation.

Fibrosis can occur in many tissues with the body, and examples include lungs (pulmonary fibrosis which includes cystic fibrosis and idiopathic pulmonary fibrosis, radiation-induced lung injury (following cancer treatment); liver (cirrhosis and bridging fibrosis); brain (glial scar); arterial stiffness, arthrofibrosis, crohn's diseases, keloid, dupuytren's contracture, mediastinal fibrosis, myelofibrosis, peyronie's disease, nephrogenic systemic fibrosis, progressive massive fibrosis, retroperitoneal fibrosis, scleroderma; myocardinal fibrosis (including interstitial fibrosis and replacement fibrosis). According to the present disclosure, the fibrosis excludes crohn's diseases.

In a further aspect, a method for decreasing the amount or the expression of fibronectin in a tissue of a subject in need thereof by administering an effective amount of a CHP to the subject is provided. In an embodiment, the subject has a fibrosis. In still an embodiment, the subject has a lung fibrosis and the tissue is a lung tissue.

In an aspect, a method for decreasing the amount or the expression of collagen 1, collagen 3, and/or collagen 4 in a tissue of a subject in need thereof by administering an effective amount of a CHP to the subject is provided. In an embodiment, the subject has a fibrosis. In still an embodiment, the subject has a lung fibrosis and the tissue is a lung tissue and the tissue is a lung tissue.

In a further aspect, a method for decreasing the amount or the expression of α-SMA in a tissue of a subject in need thereof by administering an effective amount of a CHP to the subject is provided. In an embodiment, the subject has a fibrosis. In still an embodiment, the subject has a lung fibrosis and the tissue is a lung tissue.

In an aspect, a method for decreasing the amount or the expression of TGF-β in a tissue of a subject in need thereof by administering an effective amount of a CHP to the subject is provided. In an embodiment, the subject has a fibrosis. In still an embodiment, the subject has a lung fibrosis and the tissue is a lung tissue.

In an aspect, a method for decreasing a deposit of hydroxyprolin in a tissue of a subject in need thereof by administering an effective amount of a CHP to the subject is provided. In an embodiment, the subject has a fibrosis. In still an embodiment, the subject has a lung fibrosis and the tissue is a lung tissue.

In an aspect, a method for treating a tissue fibrotic disease in a subject in need thereof comprising administering to the subject an effective amount of a CHP or a pharmaceutical composition comprising a CHP. In one embodiment, the disease is associated with liver injury, liver inflammation and/or liver fibrosis. In one embodiment, the disease is liver cirrhosis or liver fibrosis of any etiology. In one embodiment, the disease is selected from the group consisting of non-alcoholic fatty liver disease (NAFLD), non-alcoholic steatohepatitis (NASH), alcoholic fatty liver disease, alcoholic steatohepatitis, hepatic steatosis, autoimmune hepatitis, chronic hepatitis C, chronic hepatitis B, primary biliary cirrhosis, secondary biliary cirrhosis, sclerosing cholangitis, alpha-1-antitrypsin deficiency, Wilson's disease, and biliary atresia. In one embodiment, the disease is associated with lung injury, lung inflammation and/or lung fibrosis. In one embodiment, the disease is selected from the group consisting of idiopathic pulmonary fibrosis, radiation-induced pneumonitis, chronic obstructive pulmonary disease, and emphysema. In one embodiment, the disease is associated with kidney injury, kidney inflammation and/or kidney fibrosis. In one embodiment, the disease is glomerulonephritis or interstitial-tubular fibrosis.

In another aspect, the invention provides a method for treating an inflammatory disease in a subject in need thereof comprising administering to the subject an effective amount of a CHP hydrate or a pharmaceutical composition comprising the CHP hydrate. According to this aspect, the CHP hydrate is a CHP monohydrate, in particular a crystalline CHP monohydrate or a composition comprising it as described herein. In one embodiment, the disease is selected from the group consisting of alcoholic liver disease, non-alcoholic steato-hepatitis (NASH), autoimmune hepatitis, chronic hepatitis C, chronic hepatitis B, primary biliary cirrhosis, secondary biliary cirrhosis, sclerosing cholangitis, alpha-1-antitrypsin deficiency, Wilson's disease, biliary atresia, idiopathic pulmonary fibrosis, radiation-induced pneumonitis, chronic obstructive pulmonary disease, lung emphysema, lung chronic infections and/or inflammation, glomerulonephritis, interstitial-tubular fibrosis. The inventive aspect of this disclosure excludes a use of anhydrous CHP alone or with a zinc in treating inflammatory disease such as inflammatory bowel diseases, esophageal or gastro-intestinal inflammation post-radiation, inflammatory cardiomyopathy, brain inflammation post-trauma, Alzheimer's disease, encephalitis, meningitis, myositis, and arthritis.

In any of the above methods, the subject can be, e.g., human or veterinary animal or an experimental animal model.

In any of the above methods, the CHP or pharmaceutical compositions can be administered, either locally or systemically, such as by intradermal, intrathecal, intramuscular, subcutaneous, intraperitoneal or intravenous injection, but even oral, nasal, transdermal or anal administration is contemplated. In one embodiment, administration is by subcutaneous, intradermal, or intramuscular injection. In another embodiment, administration is by intraperitoneal or intrathecal administration. To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle.

For administration by inhalation, the CHP can be delivered in the form of an aerosol spray presentation from pressurized packs or a nebulizer, with the use of a suitable propellant, such as dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges for use in an inhaler or insufflator can be formulated containing a powder mix of the compound and a suitable powder base such as lactose or starch. Technologies of use include micropump nebulizers (such as the AEROGEN GO® system), jet nebulizers designed to produce large fine particle fractions (such as the PARI LC STAR®), jet nebulizers developing less shear during atomization (such as the HUDSON MICROMIST®), and ultrasonic nebulizers (such as the DeVilbiss ULTRA-NEB®).

The site of particle deposition within the respiratory tract is demarcated based on particle size. In one example, particles of about 1 to about 500 microns are utilized, such as particles of about 25 to about 250 microns, or about 10 to about 25 microns are utilized. In other embodiments, particles of about 1 to 50 microns are utilized. For use in a metered dose inhaler, for administration to lungs particles of less than about 10 microns, such as particles of about 2 to about 8 microns, such as about 1 to about 5 microns, such as particles of 2 to 3 microns, can be utilized.

The pharmaceutical compositions disclosed herein facilitate the use of a CHP to decrease fibrosis. Such a composition can be suitable for delivery of the active ingredient to any suitable subject, and can be manufactured in a manner that is itself known, e.g., by means of conventional mixing, dissolving, granulating, emulsifying, encapsulating, entrapping or lyophilizing processes. Pharmaceutical compositions can be formulated in a conventional manner using one or more pharmacologically (e.g., physiologically or pharmaceutically) acceptable carriers, as well as optional auxiliaries that facilitate processing of the active compounds into preparations which can be used pharmaceutically. Proper formulation is dependent upon the route of administration chosen. Thus, for injection, the active ingredient can be formulated in aqueous solutions. For transmucosal administration, penetrants appropriate to the barrier to be permeated are used in the formulation. Such penetrants are generally known in the art.

For oral administration, the active ingredient can be combined with pharmaceutically acceptable carriers to form tablets, pills, capsules, liquids, gels, syrups, slurries, suspensions and the like. The active ingredient can be formulated for parenteral administration by injection, such as by bolus injection or continuous infusion. Such compositions can take such forms as suspensions, solutions or emulsions in oily or aqueous vehicles, and can contain formulatory agents such as suspending, stabilizing and/or dispersing agents. Other pharmaceutical excipients are known in the art also can be included.

Single or multiple administrations of the compositions are administered depending on the dosage and frequency as required and tolerated by the subject. In one embodiment, the dosage is administered once as a bolus, but in another embodiment can be applied periodically until a therapeutic result is achieved. Generally, the dose is sufficient to treat or ameliorate symptoms or signs of disease without producing unacceptable toxicity to the subject.

In embodiments, with regard to any of the above-discussed methods, CRP may be administered to the subject in an amount from about 0.001 to about 3000 mg/kg. In some embodiments, the effective amount of the CHP may be about 0.001-0.005 mg/kg, 0.005-0.01 mg/kg, 0.01-0.02 mg/kg, 0.02-0.04 mg/kg, 0.04-0.06 mg/kg, 0.06-0.08 mg/kg, 0.08-1 mg/kg, 1-5 mg/kg, 5-6 mg/kg, 6-7 mg/kg, 7-8 mg/kg, 8-10 mg/kg, 10-15 mg/kg, 15-20 mg/kg, 20-25 mg/kg, 25-30 mg/kg, 30-35 mg/kg, 35-40 mg/kg, 40-45 mg/kg, 45-50 mg/kg, 50-100 mg/kg, 100-150 mg/kg, 150-200 mg/kg, 200-300 mg/kg, 300-400 mg/kg, 400-500 mg/kg, 500-600 mg/kg, 600-700 mg/kg, 700-800 mg/kg, 800-900 mg/kg, 900-1000 mg/kg, 1000-1100 mg/kg, 1100-1200 mg/kg, 1200-1300 mg/kg, 1300-1400 mg/kg, 1400-1500 mg/kg, 1500-1600 mg/kg, 1600-1700 mg/kg, 1700-1800 mg/kg, 1800-1900 mg/kg, 1900-2000 mg/kg, 2000-2100 mg/kg, 2100-2200 mg/kg, 2200-2300 mg/kg, 2300-2400 mg/kg, 2400-2500 mg/kg, 2500-2600 mg/kg, 2600-2700 mg/kg, 2700-2800 mg/kg, 2800-2900 mg/kg, or 2900-3000 mg/kg. The amounts are based on the amount of anhydrous CHP.

In embodiments, with regard to any of the above-discussed methods, CHP may be administered to the mammal in an amount from about 1 to about 3000 mg/day. In some embodiments, the effective amount of the CHP may be in a range of about 1-10 mg/day, 10-50 mg/day, 50-100 mg/day, 100-150 mg/day, 150-200 mg/day, 200-300 mg/day, 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-1900 mg/day, 1900-2000 mg/day, 2000-2100 mg/day, 2100-2200 mg/day, 2200-2300 mg/day, 2300-2400 mg/day, 2400-2500 mg/day, 2500-2600 mg/day, 2600-2700 mg/day, 2700-2800 mg/day, 2800-2900 mg/day, or 2900-3000 mg/day. The amounts are based on the amount of anhydrous CHP.

In embodiments, with regard to any of the above-discussed methods, an effective amount of zinc ranges from about 0.1-1 mg/day, about 1-10 mg/day, 10-50 mg/day, 50-100 mg/day, 100-150 mg/day, 150-200 mg/day, 200-300 mg/day, 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-1900 mg/day, or 1900-2000 mg/day, as calculated in term of zinc cation.

In some embodiments, for a composition comprising CHP and zinc or for an administration of a CHP-containing composition and a Zn-containing composition, the weight ratio of zinc to CRP is from about 1:10 to about 100:1 (as calculated in terms of anhydrous CRP and zinc element, unless otherwise indicated). In some embodiments, the weight ratio of zinc to CHP is from about 1:6 to about 5:1. In some embodiments, the weight ratio of zinc to CHP is from about 1:15 to about 20:1. In some embodiments, the weight ratio of zinc to CHP is from about 1:30 to about 4:1. In some embodiments, the weight ratio of zinc to CHP is from about 1:8 to about 4:1. In some embodiments, the weight ratio of zinc to CHP is from about 1:40 to about 40:1. Zinc as noted above relates to the amount of zinc cation.

As referred to herein, numerical values for zinc represent masses or concentrations of the zinc component of a zinc salt or zinc compound. Examples of zinc salts useful in connection with the invention include zinc chloride, zinc acetate, zinc gluconate, zinc stearate, zinc sulfate, zinc oxide, zinc picolinate, zinc orotate, or zinc citrate.

Certain aspects of the invention can be described in greater detail in the non-limiting Examples that follows. The following examples are included to demonstrate certain embodiments of the present disclosure. Those of skill in the art should, however, in light of the present disclosure, appreciate that modifications can be made in the specific embodiments that are disclosed and still obtain a like or similar result without departing from the spirit and scope of the intention. Therefore, all matter set forth is to be interpreted as illustrative and not in a limiting sense.

In the studies presented herein, the effects of CHP and CHP+Zn on fibrosis were evaluated. The effects of CHP and CHP+Zn on fibrosis were assessed using in vivo in bleomycin-induced pulmonary fibrosis mouse model. Surprisingly, the findings demonstrate that the CHP has an excellent anti-fibrotic activity and provide a novel therapy for fibrotic disorders.

EXPERIMENTAL EXAMPLE 1

Materials and Methods

In Vivo Analysis.

Seven-week-old male ICR mice from Koatech Co. Ltd (Gyeonggi-do, Korea). All animal experiments were approved by the Ethics Review Committee of the Advanced Bio Convergence Center, Republic of Korea. Mice were housed in specific pathogen-free conditions with a 12 hr light-dark cycle and had free access to water and food. Body weight and caloric intake were monitored throughout the experiments. The mice were housed in single cage and food intake was calculated of each animals in the cage. 5 or 25 or 50 or 100 mg/kg/day CHP monohydrate, 5 mg/kg/day CHP+10 mg/kg/day Zn, or PBS (vehicle control), was orally administered daily for 4 weeks. At the conclusion of the in vivo experiment, the mice were sacrificed and tissues were collected and weighed. Tissue samples were stored at −80° C. until analysis.

Treatment of Mice with Bleomycin and Cyclo His-Pro (CHP) Hydrate

Mice maintained under anesthesia with isoflurane were intravenously administered bleomycin 75 mg/kg in saline. The first administration of CHP hydrate or CHP hydrate+Zn was performed 30 min after bleomycin administration.

Western Blot Analysis 20-30 µg of lysates were separated on BOLT™ 4-12% Bis-Tris Plus gels with MES running buffer and transferred to nitrocellulose membranes using TRANS-BLOT® TURBO™ Transfer System (Bio-Rad). The membranes were labeled with primary antibodies, Fibronectin (1:1,000, CST), β-actin (1:2,000, CST) for overnight at 4° C. and then labeled with the horse radish peroxidase (HRP)-conjugated secondary antibodies (1:5,000, Promega). Chemiluminescence images were captured by Alliance 4.7 (UVITEC Cambridge).

Wynn and Ramalingam, Nat. Med. 18(7), pp. 1028-1040 (2012), doi:10.1038/nm.2807.

RNA Preparation and Real-Time PCR.

Total RNA was prepared by an RNeasy Mini kit (QIAGEN) according to the manufacturer's instructions. RNA integrity was assessed by an automated microfluidics-based system (Bioanalyzer 2100, Agilent, Palo Alto, CA, USA). First-strand cDNA was synthesized with the ISCRIPT™ cDNA Synthesis Kit (Bio-Rad, Hercules, CA, USA), and real-time PCR was performed using an ICYCLER™ iQ Real-Time Detection System (Bio-Rad, USA). PCR reactions were carried out with iQ SYBR GREEN SUPERMIX™ (Bio-Rad). Specific primer pairs (Genotech, Korea) are listed in Table 1. β-Aactin was used as an internal control. Amplification of real-time PCR was performed according to the protocols of Jung et al. with modification (Diabetes Obes Metab. 20(7), pp. 1688-1701 (2018), doi: 10.1111/dom.13284). The reaction was carried out at 95° C. for 3 min and followed by 39 cycles of amplification (95° C. for 10 sec, 58° C. for 10 sec, 72° C. for 30 sec). A melt curve was produced to confirm a single gene-specific peak and detect primer/dimer formation by heating the samples from 65 to 95° C. in 0.5° C. increments with a dwell time at each temperature of 10 sec while continuously monitoring fluorescence. The mRNA levels of specific genes were normalized to those of β-actin.

Hydroxyproline Assay

Collagen deposition was determined by measuring the total hydroxyproline (HYP) content, which was measured by a HYP assay kit according to the provided manufacturer's protocol. In brief, lungs were hydrolyzed at 100° C. for 40 min and mixed every 10 min. After neutralization with hydrochloric acid, the hydrolyzation products were diluted with distilled water, and assessed at 550 nm and expressed as ug/10 mg.

TABLE 1

Primer lists.

| Gene name | | Sequence |
|---|---|---|
| Collagen 1 | Forward | 5'-GCC TCA GAA GAA CTG GTA CAT-3' (SEQ ID NO: 1) |
| | Reverse | 5'-ATC CAT CGG TCA TGC TCT CT-3' (SEQ ID NO: 2) |
| Collagen 3 | Forward | 5'-AGT CAA GGA GAA AGT GGT CG-3' (SEQ ID NO: 3) |
| | Reverse | 5'-CCA GGG AAA CCC ATG ACA C-3' (SEQ ID NO: 4) |
| Collagen 4 | Forward | 5'-CGG TAC ACA GTC AGA CCA TT-3' (SEQ ID NO: 5) |
| | Reverse | 5'-CAT CAC GAA GGA ATA GCC GA-3' (SEQ ID NO: 6) |
| Fibronectin | Forward | 5'-ATG TAC CCT ATG TAC CGC TTC-3' (SEQ ID NO: 7) |
| | Reverse | 5'-GTG TGG TGG TGG TTG GAG-3' (SEQ ID NO: 8) |
| αSMA | Forward | 5'-AAT AAC ACA GAG AGA CAG ACT TG-3' (SEQ ID NO: 9) |
| | Reverse | 5'-CTT GGA TAC CCT TGG CTT TAG-3' (SEQ ID NO: 10) |
| TGFβ | Forward | 5'-CCT GAG TGG CTG TCT TTT GA-3' (SEQ ID NO: 11) |
| | Reverse | 5'-AAT CGA AAG CCC TGT ATT CCG-3' (SEQ ID NO: 12) |
| β-Actin | Forward | 5'-GCG AGA AGA TGA CCC AGA T-3' (SEQ ID NO: 132) |
| | Reverse | 5'-ATC ACG ATG CCA GTG GTA-3' (SEQ ID NO: 14) |

Statistical Methods

Statistical analyses were performed using Prism software (GRAPHPAD PRISM™ 5, La Jolla, California). Differences between multiple comparisons were analysed by ANOVA, followed by Tukey's post hoc test. P values less than 0.05 were considered statistically significant.
RESULTS: CHP Protects Against Bleomycin (BLM)-Induced Pulmonary Fibrosis.

Figure 2:
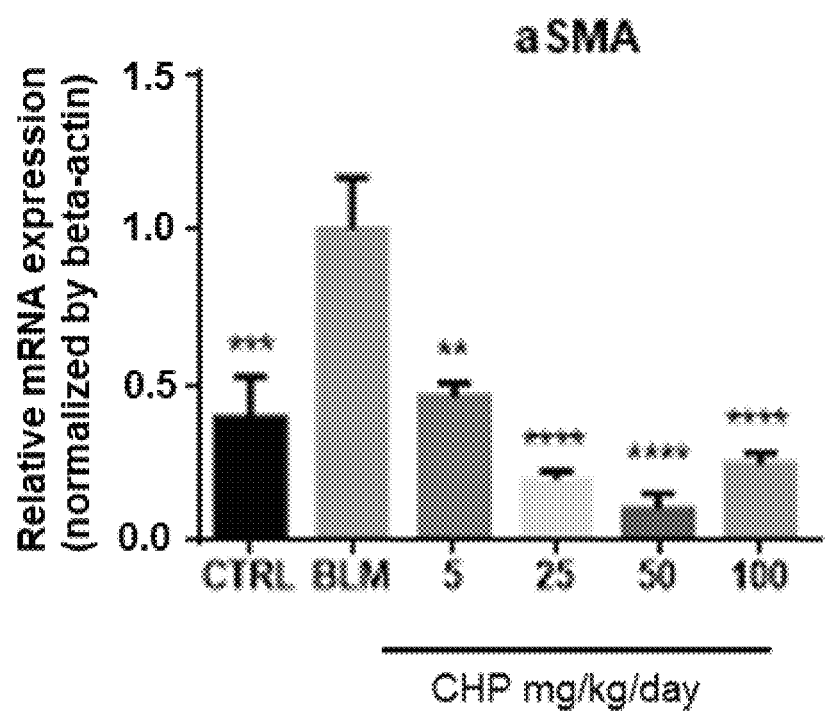
FIG. 2 shows the relative mRNA expression levels of α-smooth muscle actin (aSMA) in bleomycin (BLM)-induced pulmonary fibrosis ICR mice. The fibronectin mRNA expression level (BLM bar) in the ICR mice injected with bleomycin to induce pulmonary fibrosis is set 1.0. CTRL is a control mice which did not receive bleomycin. 5, 25, 50, and 100 mg/kg CHP bars show the relative aSMA mRNA expression levels in the BLM-injected ICR mice. The results show that 5, 25, 50, and 100 mg/kg CHP significantly reduces the αSMA expression in pulmonary fibrosis animal model.
Figure 3:
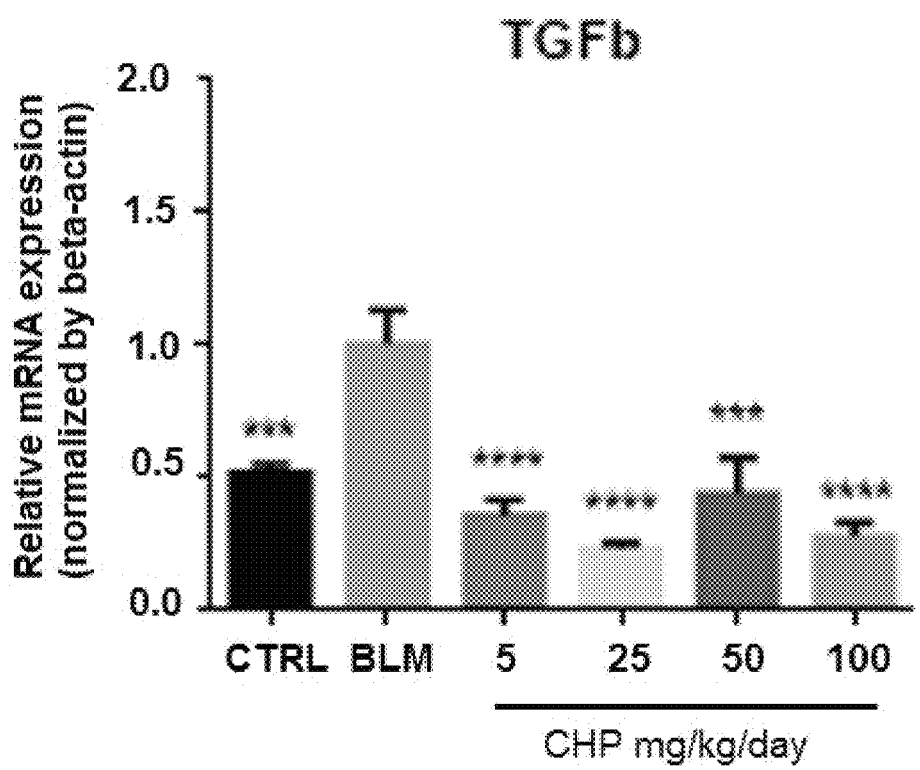
FIG. 3 shows the relative mRNA expression levels of transforming growth factor-β (TGF-β) in bleomycin (BLM)-induced pulmonary fibrosis ICR mice. The fibronectin mRNA expression level (BLM bar) in the ICR mice injected with bleomycin to induce pulmonary fibrosis is set 1.0. CTRL is a control mice which did not receive bleomycin. 5, 25, 50, and 100 mg/kg CHP bars show the relative TGF-β mRNA expression levels in the BLM-injected ICR mice. The results show that 5, 25, 50, and 100 mg/kg CHP significantly reduces the TGF-β expression in pulmonary fibrosis animal model.
Figure 4:
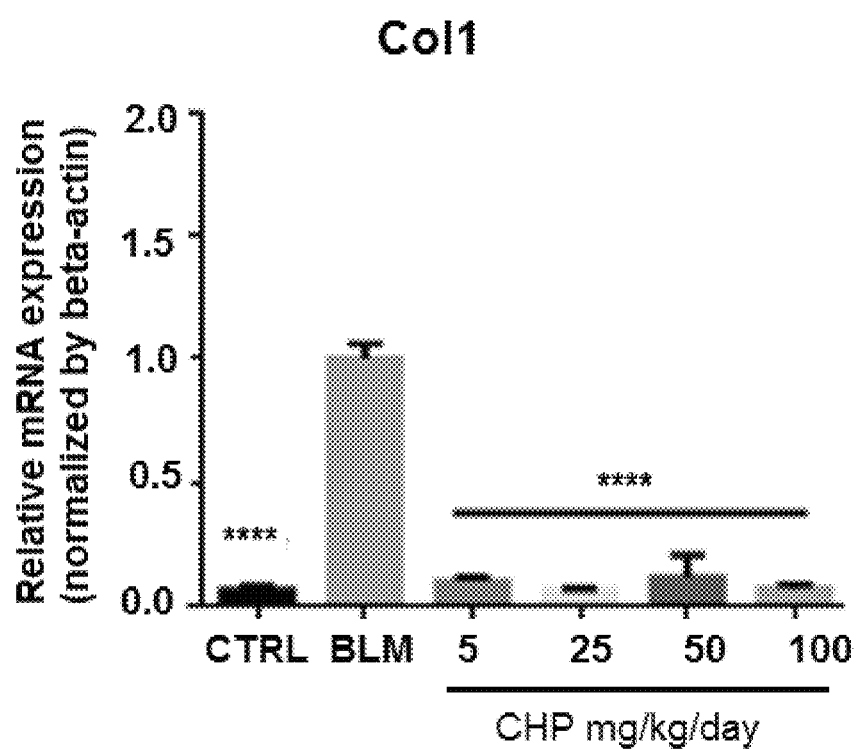
FIGS. 4-6 show the relative mRNA expression levels of Type 1, 3, and 5 collagens (Col1, Col3, Co4), respectively, in bleomycin (BLM)-induced pulmonary fibrosis ICR mice. The fibronectin mRNA expression level (BLM bar) in the ICR mice injected with bleomycin to induce pulmonary fibrosis is set 1.0. CTRL is a control mice group which did not receive bleomycin. 5, 25, 50, and 100 mg/kg CHP bars show the relative Col1, Col3, and Col4 mRNA expression levels in the BLM-injected ICR mice. The results show that 5, 25, 50, and 100 mg/kg CHP significantly reduces the collagen expressions in pulmonary fibrosis animal model.
Figure 5:
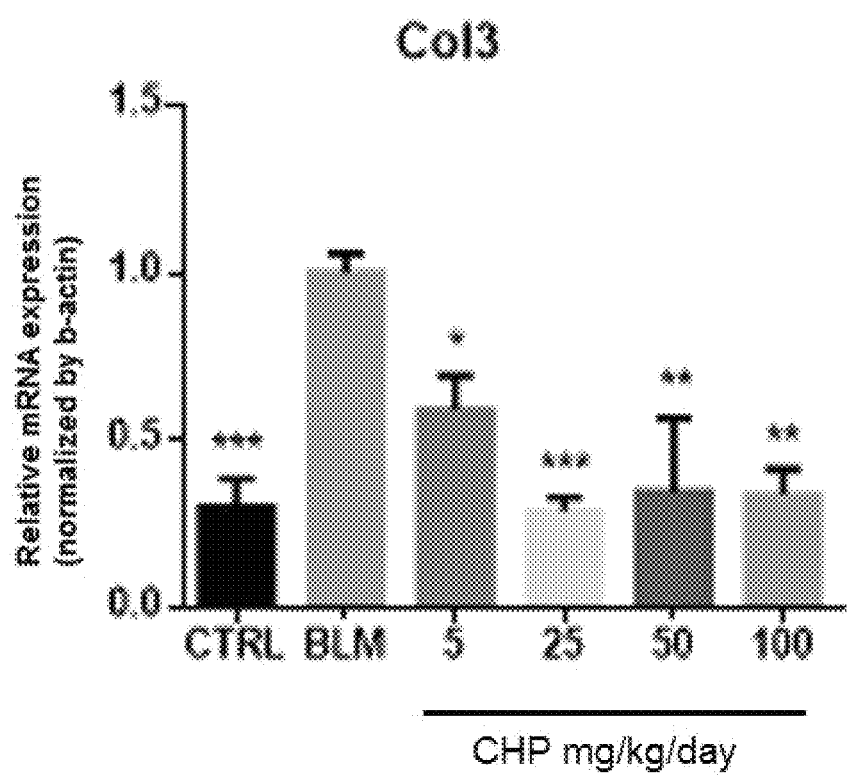
Figure 6:
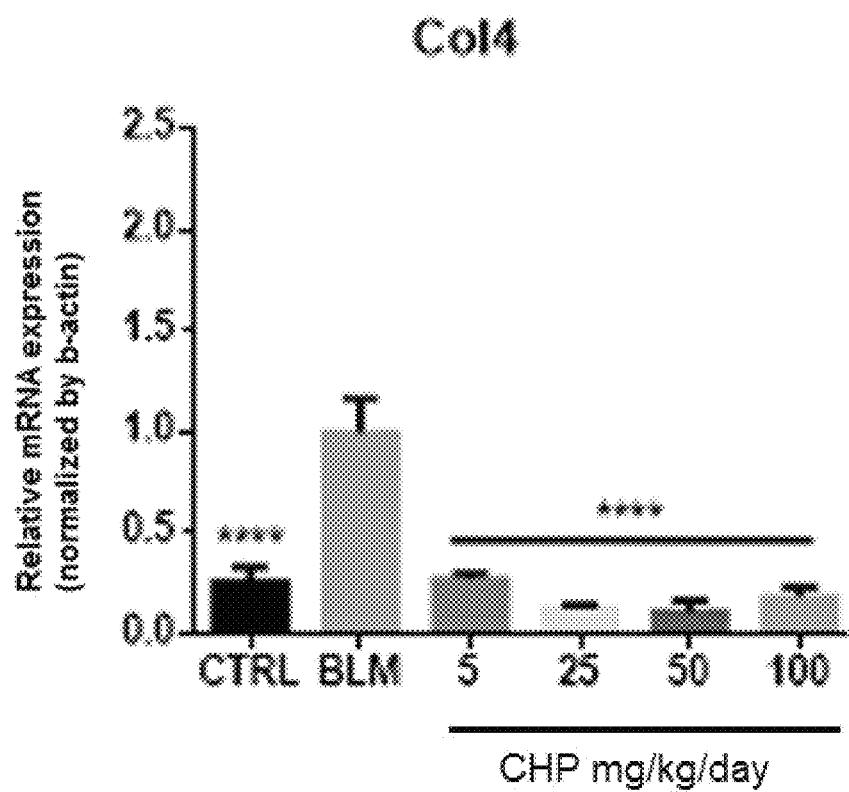
Figure 7:
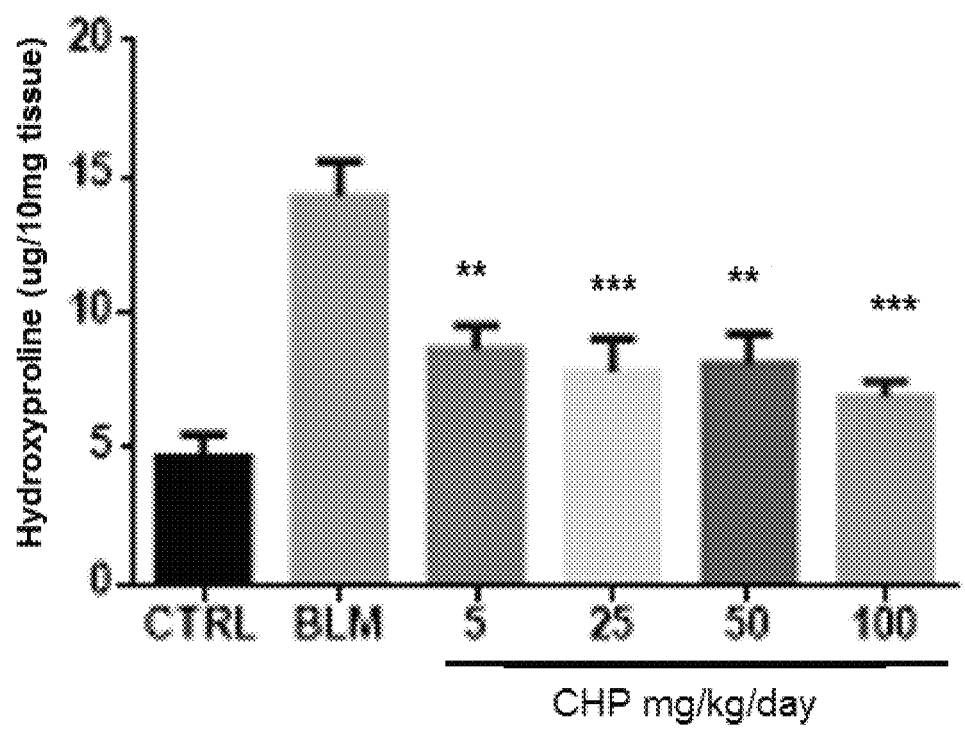
FIG. 7 shows the lung hydroxyproline amounts in control mice (CTRL), bleomycin-induced IPF mice (BLM), and bleomycin-induced IPF mice which received 5, 25, 50, or 100 mg/kg of CHP. The results show that 5, 25, 50, and 100 mg/kg CHP significantly reduces the accumulation of collagen in the lung of IPF mice.
Figure 8:
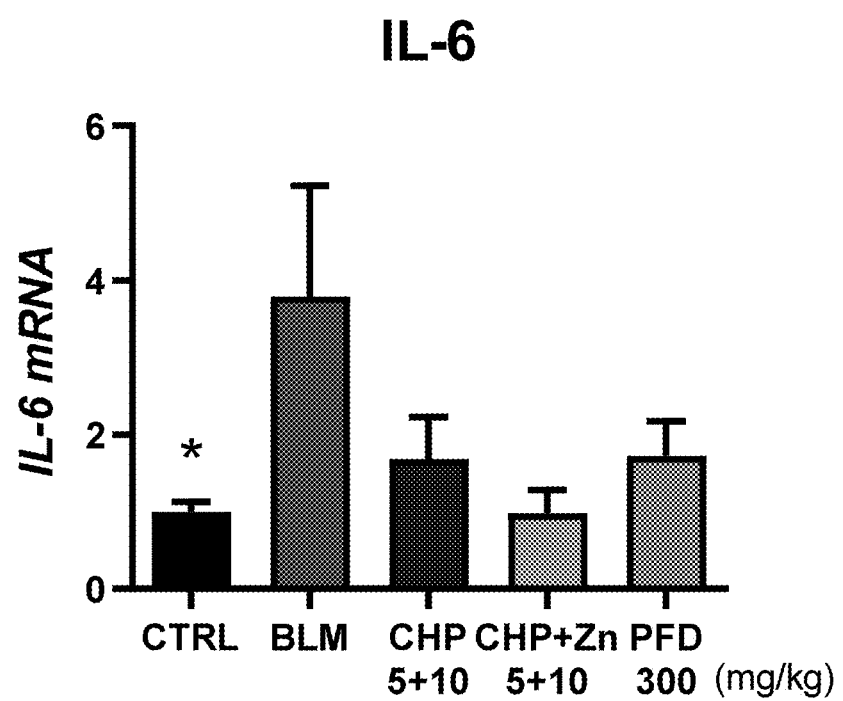
FIGS. 8-13 show the relative mRNA expression levels of IL-6, Type 1, 3, 5 collagens (Col1, Col3, Col4), and fibronectin, respectively, and the fibronectin expression, in bleomycin (BLM)-induced pulmonary fibrosis ICR mice. The fibronectin mRNA expression level (BLM bar) in the ICR mice injected with bleomycin to induce pulmonary fibrosis is set 1.0. CTRL is a control mice group which did not receive bleomycin and PFD (300 mg/kg) is a positive control. CHP (5 mg/kg) and CHP+Zn (5+10 mg/kg) bars show the relative IL-6, Col1, Col3, Col4, and fibronectin mRNA expression levels and fibronectin expression level in the BLM-injected ICR mice.
Figure 9:
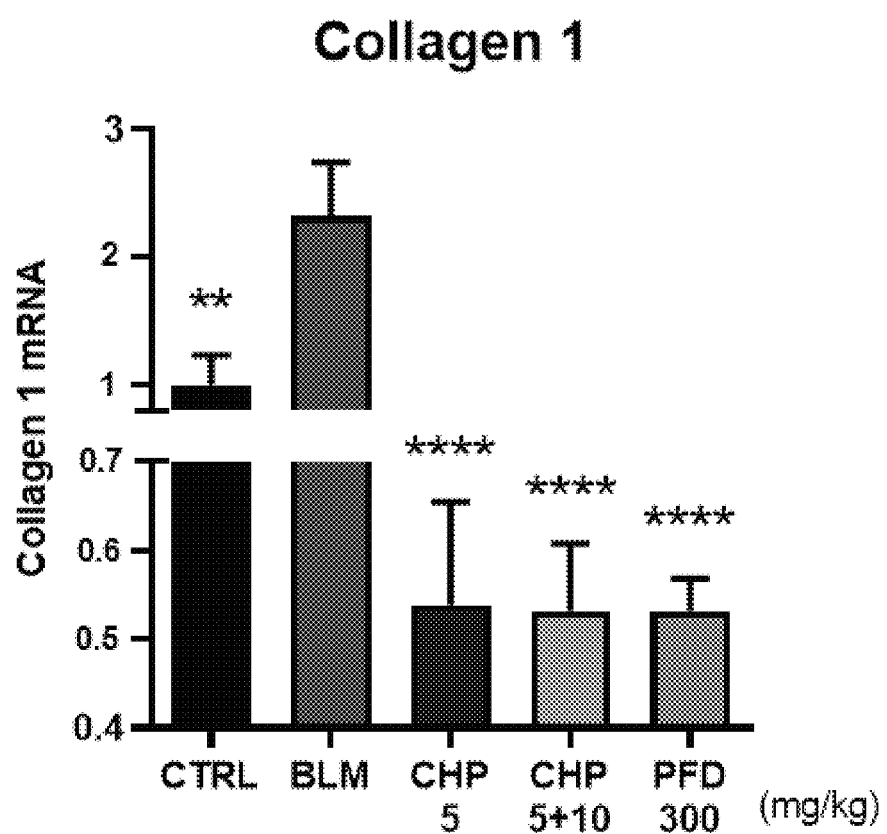
Figure 10:
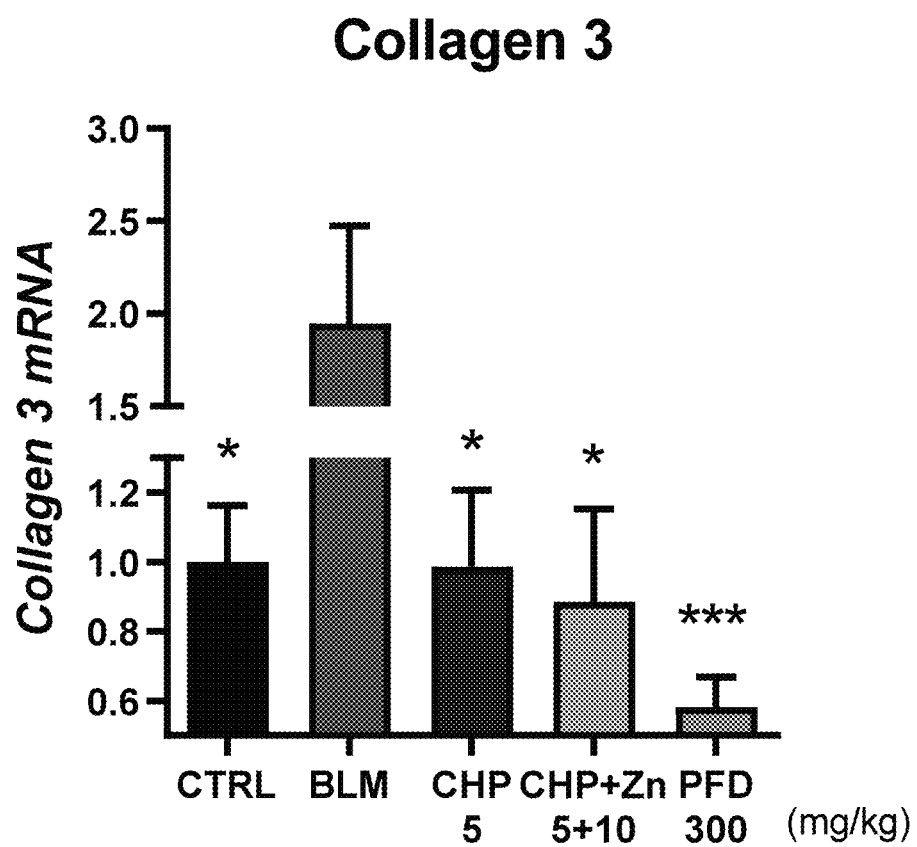
Figure 11:
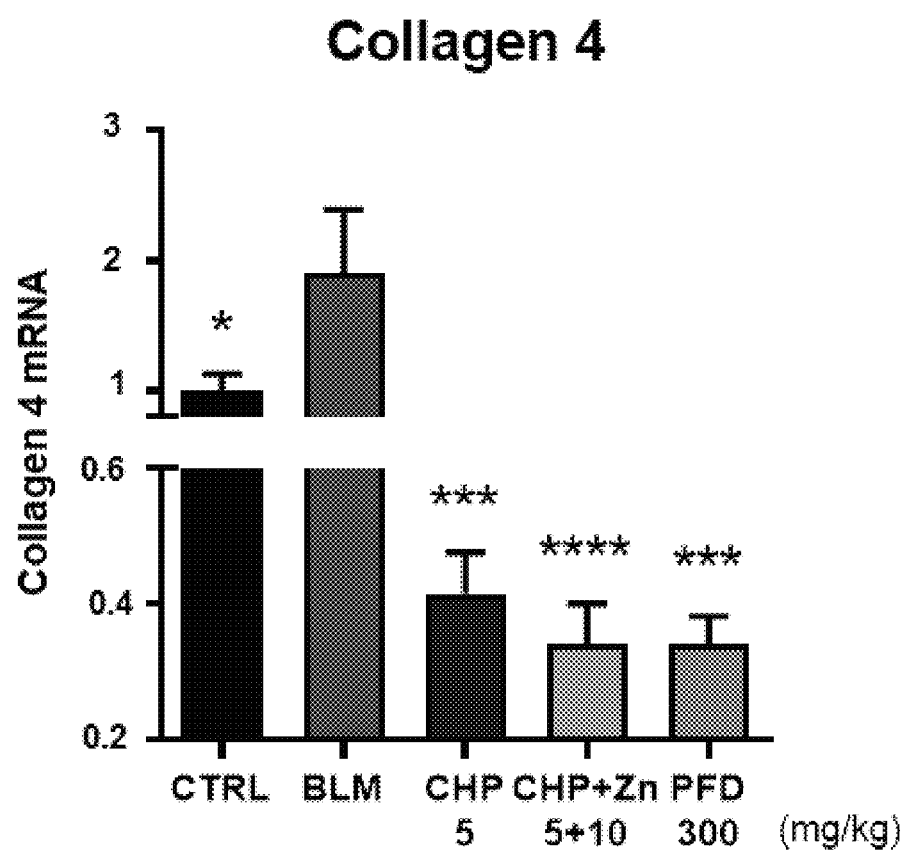
Figure 12:
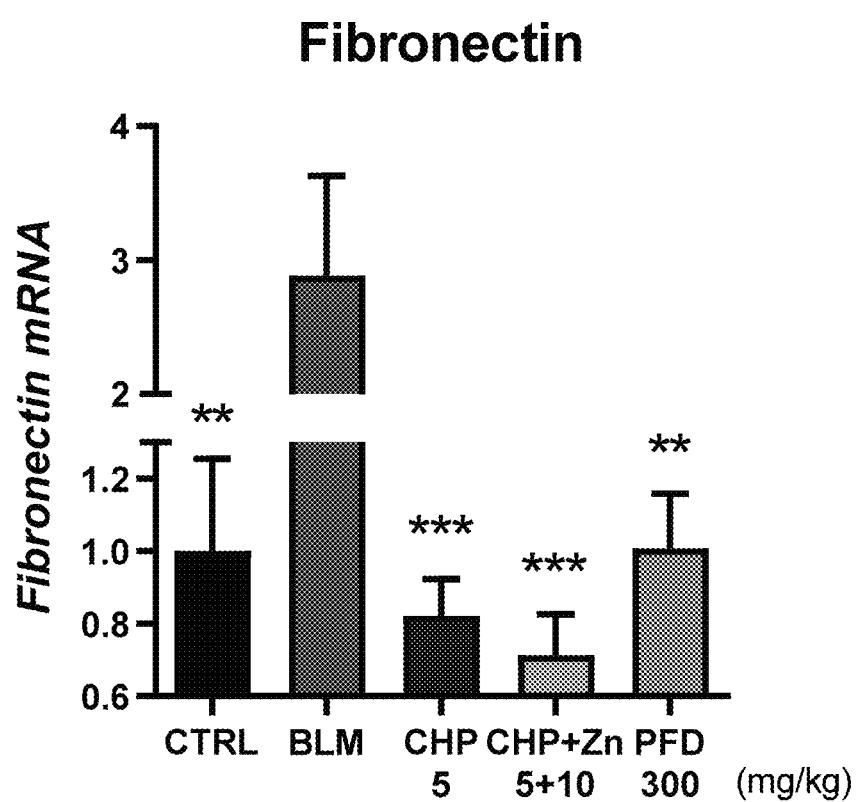
Figure 13:
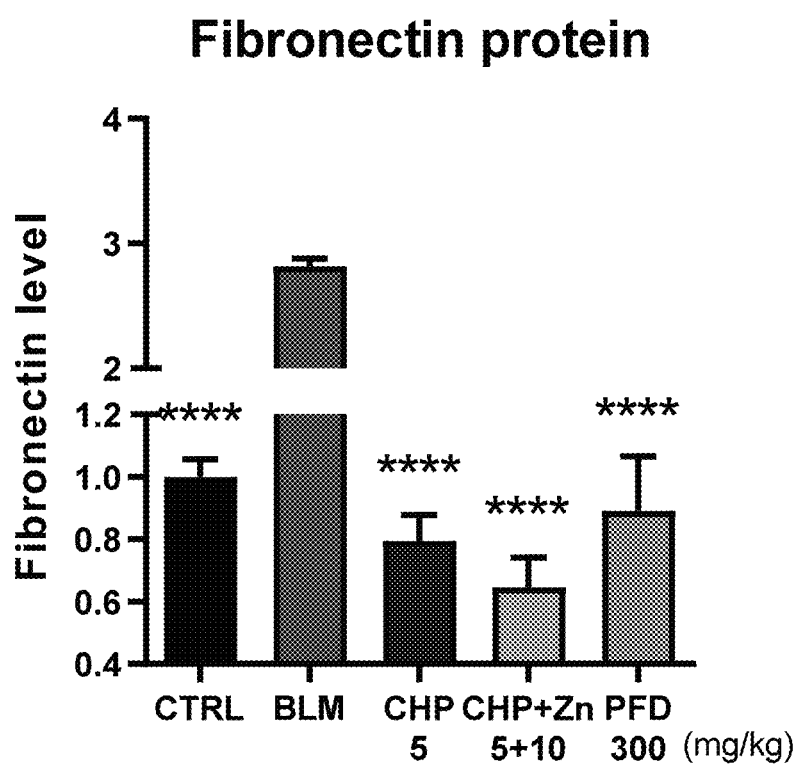
Figure 14:
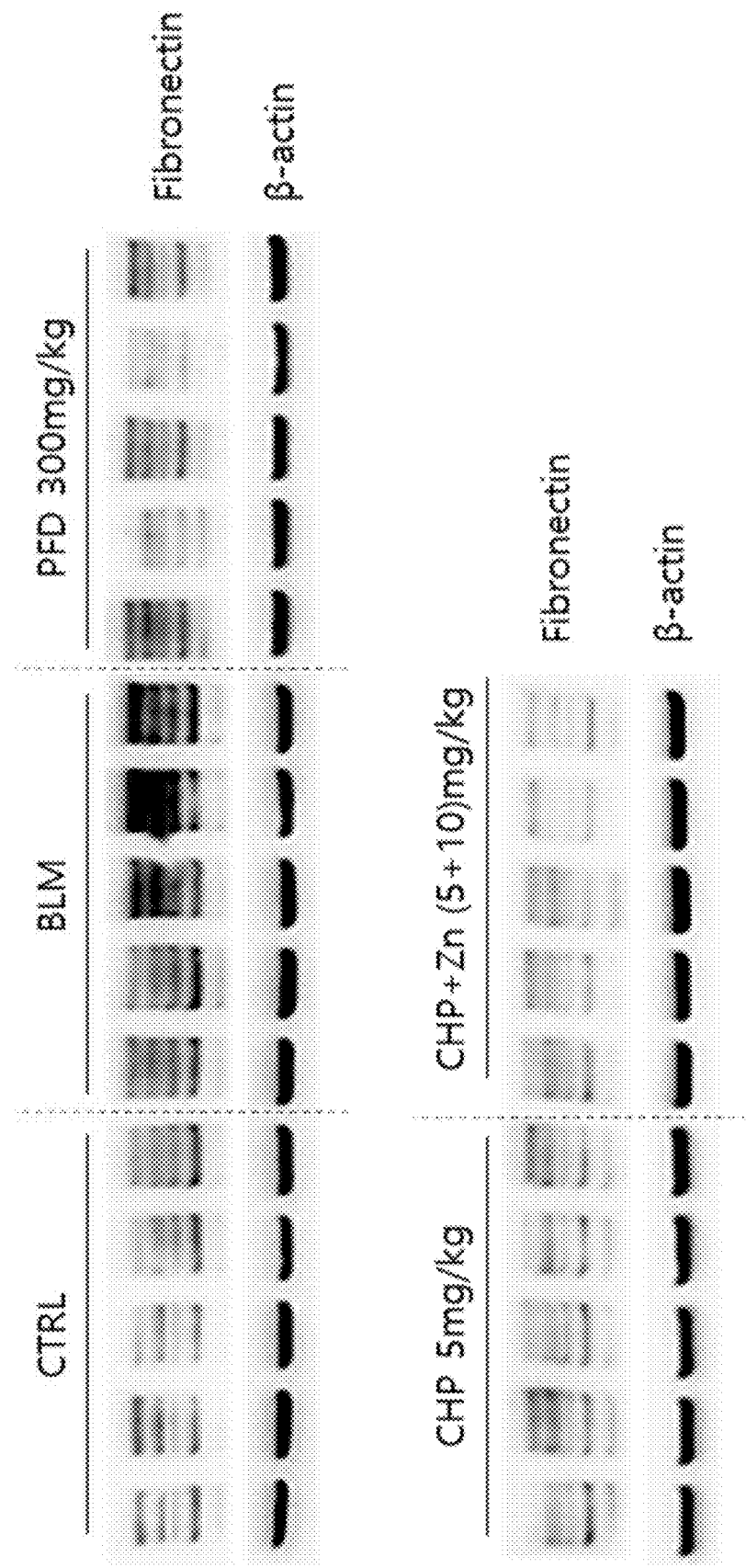
FIG. 14 shows the Western blot results for fibronectin and beta-actin expression in the ICR mice injected with bleomycin to induce pulmonary fibrosis. CTRL is a control mice group which did not receive bleomycin, BLM is a mice group received bleomycin only, and PFD (300 mg/kg) is a positive control. CHP (5 mg/kg) and CHP+Zn (5+10 mg/kg) are the ICR mice group injected with bleomycin and the CHP or CHP+Zn.

The results are shown in FIGS. 1-14.

Idiopathic pulmonary fibrosis (IPF) is a chronic pulmonary disorder of unknown etiology and is characterized by progressive deposition of extracellular matrix (ECM) proteins such as collagen and fibronectin.

ICR mice are more susceptible to BLM induced fibrosis and widely used for assessing anti-fibrosis activity and studying fibrosis mechanisms. As evidenced by FIGS. 1-7, the inflammation and fibrosis biomarkers as well as hydroxyproline (HYP) content in CHP hydrate-treated groups were significantly decreased compared to BLM alone group. In addition, the expression of a-SMA (a hallmark of myofibroblasts), Col I, Col III, Col IV mRNA levels were also dramatically reduced in CHP hydrate-treated mice compared to the BLM alone group. See, FIGS. 1-7. Further, Western blotting analysis showed that fibronectin protein levels were also dramatically reduced in CHP-treated mice compared to BLM group. The combination group of CHP with zinc showed a decrease in IL-6, Col III, Col IV, fibronectin mRNA levels and fibronectin protein levels compared to the CHP alone group. And both the CHP+zinc group and the CHP alone group had a similar effect to Pirfenidone (PFD) at 300 mg/kg as a positive control. See, FIGS. 8-14.

Taken together, these results confirm that CHP could effectively ameliorate inflammation and fibrosis in a tissue (e.g., lung tissue).

EXPERIMENTAL EXAMPLE 2

ICR mice are administered with bleomycin as described above in EXPERIMENTAL EXAMPLE 1. On day-10, once the fibrotic reaction is established, mice are received a CHP hydrate i) intraperitoneally (IP) at amount 5, 25, 50, or 100 μg/kg on days 10, 17 and 24); or ii) by inhalation (mean particle size of about 1 μm) at amount of 250, 500, 800, or 1200 μg on days 10, 17 and 24; and iii) by intratracheal instillation at an amount 100 μg of CHP monohydrate on days 10, 17 and 24. The inhalation (ii) parameters are as follows:

Pari disperse rate(ml/min): 0.25
Pari Flow rate(L/min): 5.5
Aerosol concentration (mg/L): 1
RMV(L/min): 0.002
CHP inhaled per day (μg): 250, 500, 800, or 1200
Exposure duration per day: 30-40 min Control groups are received sterile water alone. BLM groups are received only bleomycin without a CHP hydrate. Animals are sacrificed on day 27. The mRNA levels of α-SMA, fibronectin, Col I, Col III, Col IV, and TGF-β in the lung are determined, and the amount of hydroxyprolin in lung tissue is determined.

The specific pharmacological and biochemical responses observed in the assays described may vary according to and depending on the particular active compound selected or whether there are present pharmaceutical carriers, as well as tire type of formulation and mode of administration employed, and such expected variations or differences in the results are contemplated in accordance with practice of the present invention.

All patents, applications, publications, test methods, literature, and other materials cited herein are hereby incorporated by reference in their entirety as if physically present in this specification.

The invention claimed is:

1. A method for treating fibrosis comprising administering an effective amount of a composition comprising a cyclo(His-Pro) hydrate to a subject in need thereof, wherein the fibrosis is idiopathic pulmonary fibrosis.

2. The method of claim 1, wherein the composition further comprises zinc.

3. The method of claim 2, wherein the zinc is zinc ion, zinc metal, or a zinc salt selected from the group consisting of zinc chloride, zinc acetate, zinc gluconate, zinc stearate, zinc sulfate, zinc oxide, zinc picolinate, zinc orotate, and zinc citrate.

4. The method of claim 1, wherein the effective amount of the cyclo(His-Pro) hydrate is in a range of about 1-10 mg/day, 10-50 mg/day, 50-100 mg/day, 100-150 mg/day, 150-200 mg/day, 200-300 mg/day, 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-1900 mg/day, 1900-2000 mg/day, 2000-2100 mg/day, 2100-2200 mg/day, 2200-2300 mg/day, 2300-2400 mg/day, 2400-2500 mg/day, 2500-2600 mg/day, 2600-2700 mg/day, 2700-2800 mg/day, 2800-2900 mg/day, or 2900-3000 mg/day, as calculated in terms of anhydrous cyclo(His-Pro).

5. The method of claim 1, wherein the effective amount of the cyclo(His-Pro) hydrate is in a range of about 0.001-0.005 mg/kg, 0.005-0.01 mg/kg, 0.01-0.02 mg/kg, 0.02-0.04 mg/kg, 0.04-0.06 mg/kg, 0.06-0.08 mg/kg, 0.08-1 mg/kg, 1-5 mg/kg, 5-6 mg/kg, 6-7 mg/kg, 7-8 mg/kg, 8-10 mg/kg, 10-15 mg/kg, 15-20 mg/kg, 20-25 mg/kg, 25-30 mg/kg, 30-35 mg/kg, 35-40 mg/kg, 40-45 mg/kg, 45-50 mg/kg, 50-100 mg/kg, 100-150 mg/kg, 150-200 mg/kg, 200-300 mg/kg, 300-400 mg/kg, 400-500 mg/kg, 500-600 mg/kg, 600-700 mg/kg, 700-800 mg/kg, 800-900 mg/kg, 900-1000 mg/kg, 1000-1100 mg/kg, 1100-1200 mg/kg, 1200-1300 mg/kg, 1300-1400 mg/kg, 1400-1500 mg/kg, 1500-1600 mg/kg, 1600-1700 mg/kg, 1700-1800 mg/kg, 1800-1900 mg/kg, 1900-2000 mg/kg, 2000-2100 mg/kg, 2100-2200 mg/kg, 2200-2300 mg/kg, 2300-2400 mg/kg, 2400-2500 mg/kg, 2500-2600 mg/kg, 2600-2700 mg/kg, 2700-2800 mg/kg, 2800-2900 mg/kg, or 2900-3000 mg/kg, as calculated in terms of anhydrous cyclo(His-Pro).

6. The method of claim 1, wherein the composition is a solid composition that consists essentially of (i) the cyclo(His-Pro) hydrate, or (ii) the cyclo(His-Pro) hydrate and a zinc.

7. The method according to claim 1, wherein the administering of the composition comprising a cyclo(His-Pro) hydrate as an active ingredient:
(a) reduces expression of transforming growth factor-β (TGF-β) in the lung of the target subject;
(b) reduces expression of α-smooth muscle actin (α-SMA) in the lung of the subject;
(c) reduces expression of fibronectin in the lung of the subject;
(d) reduces expression of collagen 1 in the lung of the subject;
(e) reduces expression of collagen 3 in the lung of the subject; and/or
(f) reduces expression of collagen 4 in the lung of the subject.

8. The method of claim 1, wherein the composition is a solid composition and the cyclo(His-Pro) hydrate is a crystalline cyclo(His-Pro) hydrate.

9. The method of claim 8, the crystalline cyclo(His-Pro) hydrate is characterized by an X-ray powder diffraction (XRPD) diffractogram comprising peaks at 2θ values of 13.7°±0.2°, 17°±0.2°, and 27.3°±0.2.

10. The method of claim 9, wherein the XRPD diffractogram further comprises a peak at 2θ value of 10°±0.2°.

11. The method of claim 1, which further comprises administering a zinc to the subject.

12. The method of claim 1, wherein the zinc is administered to the subject in an amount ranging from about 0.1-1 mg/day, 1-10 mg/day, 10-50 mg/day, 50-100 mg/day, 100-150 mg/day, 150-200 mg/day, 200-300 mg/day, 300-400 mg/day, 400-500 mg/day, 500-600 mg/day, 600-700 mg/day, 700-800 mg/day, 800-900 mg/day, 900-1000 mg/day, 1000-1100 mg/day, 1100-1200 mg/day, 1200-1300 mg/day, 1300-1400 mg/day, 1400-1500 mg/day, 1500-1600 mg/day, 1600-1700 mg/day, 1700-1800 mg/day, 1800-1900 mg/day, or 1900-2000 mg/day, as calculated in terms of zinc cation.

13. The method of claim 1, wherein the zinc is zinc ion, zinc metal, or a zinc salt selected from the group consisting of zinc chloride, zinc acetate, zinc gluconate, zinc stearate, zinc sulfate, zinc oxide, zinc picolinate, zinc orotate, and zinc citrate.

* * * * *